(12) United States Patent
Woerdeman et al.

(10) Patent No.: US 7,520,929 B2
(45) Date of Patent: Apr. 21, 2009

(54) GLUTEN BIOPOLYMERS

(75) Inventors: Dara Woerdeman, Falls Church, VA (US); Wim Veraverbeke, Heverlee (BE); Ignace Verpoest, Kessel-Lo (BE); Jan Delcour, Heverlee (BE); Richard S. Parnas, West Hartford, CT (US)

(73) Assignees: K.U. Leuven Research & Development, Leuven (BE); University of Connecticut, Farmington, CT (US)

( * ) Notice: Subject to any disclaimer, the term of this patent is extended or adjusted under 35 U.S.C. 154(b) by 690 days.

(21) Appl. No.: 10/529,459

(22) PCT Filed: Sep. 26, 2003

(86) PCT No.: PCT/BE03/00163

§ 371 (c)(1),
(2), (4) Date: Jun. 27, 2005

(87) PCT Pub. No.: WO2004/029135

PCT Pub. Date: Apr. 8, 2004

(65) Prior Publication Data

US 2006/0042506 A1 Mar. 2, 2006

(30) Foreign Application Priority Data

Sep. 26, 2002 (GB) ................... 0222257.8
Aug. 8, 2003 (GB) ................... 0318775.4

(51) Int. Cl.
*C08L 89/00* (2006.01)
*C09D 189/00* (2006.01)
(52) U.S. Cl. .................... 106/154.2; 530/374
(58) Field of Classification Search ............. 106/154.2; 530/374
See application file for complete search history.

(56) References Cited

U.S. PATENT DOCUMENTS

| 5,665,152 | A | 9/1997 | Bassi et al. |
| 6,045,868 | A | 4/2000 | Hernandez et al. |
| 2006/0027941 | A1* | 2/2006 | Woerdeman ................ 264/129 |
| 2008/0105998 | A1* | 5/2008 | Woerdeman et al. ........ 264/239 |

FOREIGN PATENT DOCUMENTS

WO    WO 02/059212 A    8/2002

* cited by examiner

*Primary Examiner*—David M Brunsman
(74) *Attorney, Agent, or Firm*—Clark & Elbing LLP

(57) ABSTRACT

This invention consists of a modified gluten biopolymer for use in industrial applications, such as composites and foams. In the present work, the fracture toughness of the gluten polymer was improved with the addition of a thiol-containing modifying agent. This work also resulted in the development of a gluten biopolymer-modified fiber bundle, demonstrating the potential to process fully biodegradable composite materials. Qualitative analysis suggests that a reasonably strong interface between the natural fibers and biopolymer matrix can form spontaneously under the proper conditions. Therefore this invention relates to a modified gluten biopolymer for use in industrial applications, such as composites, stabilized foams and molded articles of manufactures. The present invention relates to a new gluten based biopolymer with modified properties, such as an increase in impact strength, and prepared by using thiol-containing molecules. The multifunctional activity of the polythiol-containing molecules generates the potential for the development of a new material base for commodity plastics. The invention furthermore relates to a new composite material comprising gluten-coated fiber, its use and the method for preparing the composite material.

18 Claims, 16 Drawing Sheets

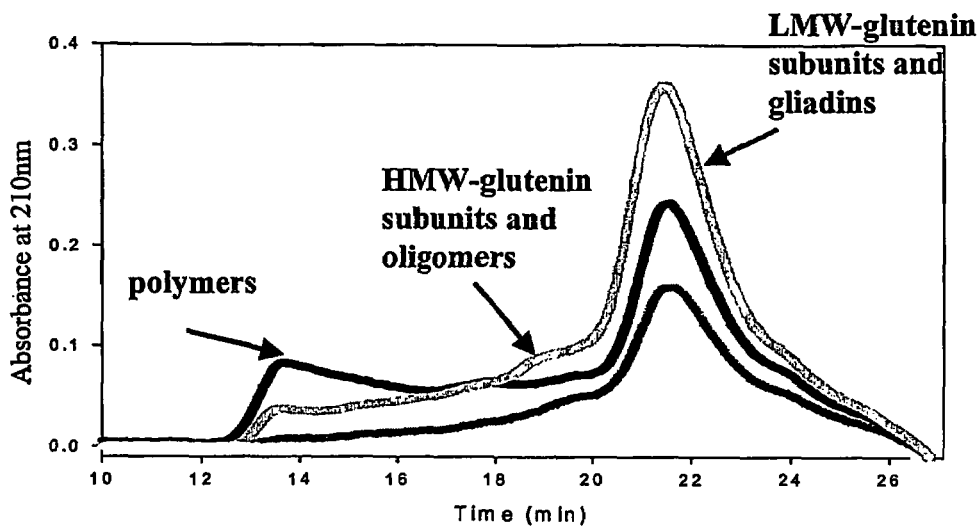

From top to bottom at the peak around 21 min.:
- thiol-modified gluten (sample 22) before molding
- native gluten (sample 20) before molding
- native gluten (sample 20) after molding
- thiol-modified gluten (sample 22) after molding

Fig 8 a.

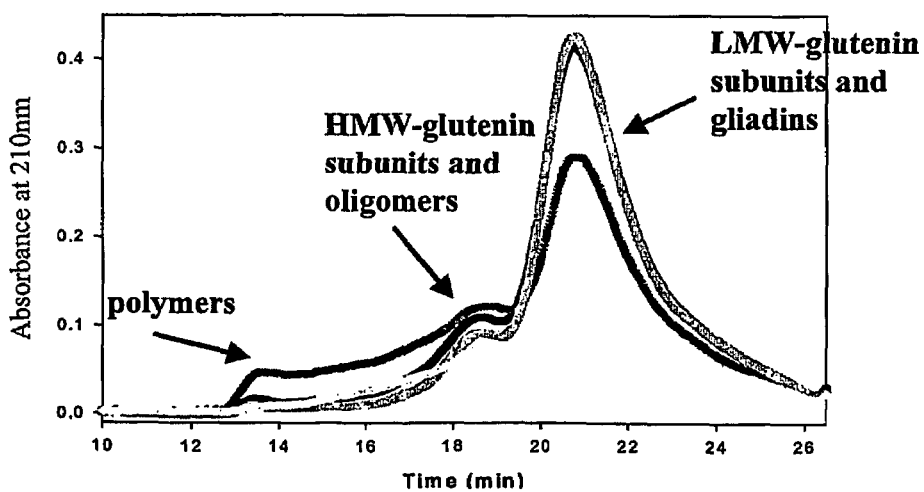

From top to bottom at the peak around 21 min.:
- thiol-modified gluten (sample 22) before molding
- native gluten (sample 20) before molding (practically converged with upper curve)
- native gluten (sample 20) after molding
- thiol-modified gluten (sample 22) after molding

Fig. 8 b.

Breaking Strain

Strength

Stiffness

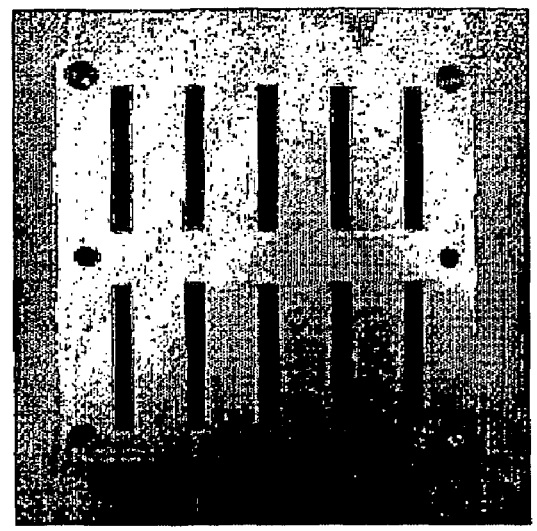
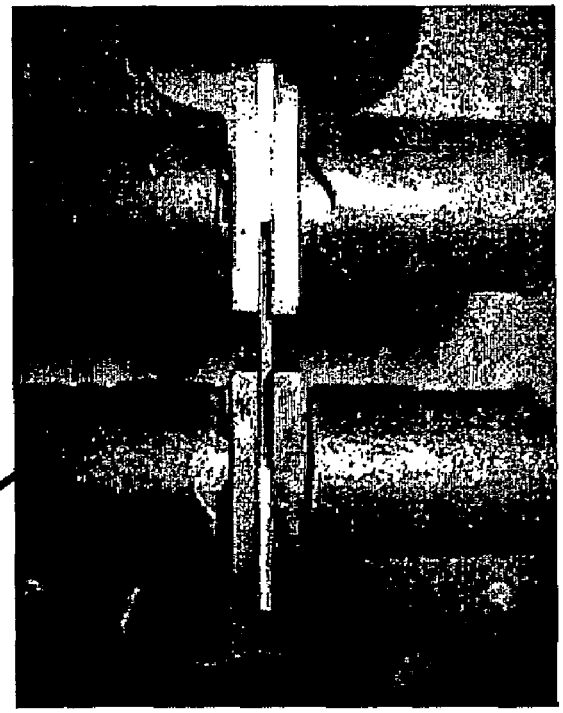
Fig. 13

GLUTEN BIOPOLYMERS

CROSS REFERENCE TO RELATED APPLICATIONS

This application is the U.S. National Stage of International Application No PCT/BE2003/000163, filed Sep. 26, 2003, which, in turn, claims the benefit of GB 0222257.8 and GB 0318775.4 filed Sep. 26, 2002 and Aug. 8, 2003, respectively.

FIELD OF THE INVENTION

This application is a 371 of PCT/BE03/00163, filed 26 Sep. 2003.

The present invention relates to a new gluten based biopolymer with modified properties, like an increased impact strength, and prepared by using polythiol-containing molecules. This invention also relates to a modified gluten biopolymer for use in industrial applications, such as composites, stabilized foams and molded articles of manufactures and to the process for preparing the new gluten based biopolymer. The invention furthermore relates to a new composite material comprising gluten-coated fiber, its use and the process for preparing the composite material.

BACKGROUND OF THE INVENTION

Current polymer production often involves the use of toxic solvents, which place workers at risk, damages the environment, and places a large regulatory burden on government and companies alike. Water-based or solid powder-based production of biopolymers and composites could provide enormous reductions in the toxic solvent load on workers and the surrounding environment. This increased (environmental) awareness has given the materials community impetus to develop cost-effective biomaterials with adequate mechanical properties. While research in recent years has led to an improved understanding of the properties of natural fibers, the problem of identifying a cost-effective biopolymer matrix material or composite material with suitable properties remains unresolved.

Plant proteins, such as for example wheat proteins, are interesting renewable raw materials and already a wide variety of biopolymers based on plant proteins has been used and investigated, alone or in mixtures, in order to obtain for example edible films and coatings. The plant proteins investigated include soy proteins, corn zein, wheat proteins, cotton seed proteins and pea proteins and can be considered as heteropolymers.

Wheat gluten is a mixture of monomeric proteins (gliadins) and "polymerized" proteins (glutenins) linked through intermolecular disulfide bridges. The gluten proteins are largely implicated in the viscoelastic character of gluten and gluten proteins are responsible for giving wheat flour dough its strength and visco-elastic properties. Wheat gluten can easily be isolated by removing starch and water solubles by gently working a dough under a small stream of water. After washing, a rubbery ball is left, which is called gluten. Next to this process which is called "dough or Martin process" other isolation methods exist like the "batter process". Commercially available gluten contain approximately 75% protein, 10% carbohydrate, <10% moisture, 5% lipids and <1% minerals, but these amounts are variable. The gluten proteins are furthermore very rich in glutamine and proline.

There is already much literature on the use of gluten, also in industrial applications. For example wheat gluten films have been studied in significant detail (Gennadios, A., and Weller, C. L., *Food Technol.* 1990, 44, 63-69; Gontard, N., et al., *J. Food Sci.* 1992, 57, 190-195; Herald, T. J., et al., *J. Food Sci.* 1995, 60, 1147-1150; Roy, S. et al., *J. Food Sci.* 1999, 64, 57-60; Larré, C., et al., J. Agric. Food Chem. 2000, 48, 5444-5449). Many attempts have been made to convert wheat gluten or corn zein into a usable biodegradable polymer (Guilbert, S. et al., *Food Add. Contam.* 1997, 14, 741; Pommet, M. et al., *Polymer* 2003, 44, 115; Redl, A. et al., *Rheol. Acta* 1999, 38, 311; Pouplin, M. et al., *Agric. Food Chem.* 1999, 47(2), 538-543; di Giola, L. et al., *Agric. Food Chem.* 1999, 47, 1254). Films have been cast from gluten protein dispersions in water under different pH conditions or in ethanol. It was demonstrated that plasticizing agents could be used to improve film flexibility and decrease brittleness (Ali, Y et al. *Ind. Crops Prod.* 1997, 6, 177-184). Indeed, researchers have observed that the preparation of wheat gluten films necessitates the use of a plasticizer. In the absence of a plasticizer, gluten films are brittle and difficult to handle. A number of plasticizers have been explored in the past, including amines (diethanolamine and triethanolamine) and polyhydroxy compounds (anhydrous glycerol, polyethyleneglycols, and polypropyleneglycols). Typical concentrations range from 10 g to 60 g/100 g of dry matter (Gennadios, A. and Weller, C. L., *Food Technol.* 1990, 44, 63-69; Roy, S. et al., *J. Food Sci.* 1999, 64, 57-60). From three known plasticizers (water, glycerol and sorbitol), water was found to be the most effective plasticizer (Pouplin, M., et al., *J. Agric. Food Chem.* 1999, 47, 538). The action of a plasticizer is generally to interpose itself between the polymer chains and alter the force holding the chains together. Polymer plasticization enables thus to reduce the shaping temperature of the thermoplastic process and to impart adequate flexibility to the material. However, it can also greatly influence the functional properties of the material (Pommet, M. et al., *Polymer* 2003, 44, 115). In a more recent study, Pommet et al. explored the use of fatty acids as a plasticizing agent for gluten (Pommet, M., Redl, A., Morel, M. H., Guilbert, S., *Polymer* 2003, 44, 115). Their thermomechanical data revealed a "compatibility limit" between the lipid and gluten, beyond which phase separation was observed.

The prior art describes methods for fractionating gluten into gliadin and glutenin (Midwest Grain U.S. Pat. No. 5,610, 277) and attempts to form solid, non-edible biodegradable, grain-protein based articles (Midwest Grain U.S. Pat. No. 5,665,152), where the processes applied always involves cleaving of the disulfide linkages in the protein using at least 0.01 by weigth of a reducing agent, selected from sodium sulfite, sodium bisulfite, sodium metabisulfite or ascorbic acid and respectively furthermore selected from alkali metal and ammonium sulfites, nitrites, mercaptoethanol, cysteine, cysteamine and mixtures thereof. The formulation of U.S. Pat. No. 5,610,277 also includes from about 20-85% by weigth of grain protein, from about 5-75% by weigth starch, up to about 14% by weigth water and from about 10-40% by weight of a plasticizer, such as glycerol. In the U.S. patent, also the mixing with fibers is described. While some aspects of the work by Midwest Grain appear similar to our work, there are however several distinct differences. That is, the additive we propose in first instance not only reduces a number of the disulfide linkages in the protein, but they also have the potential to be covalently incorporated in the protein polymer network and crosslinking the proteins, thereby modifying the polymer network and as a consequence modifying the material properties.

It can be argued that the formation of covalent bonds is a necessary first step in the development of a stable biopolymer system. Most of the studies presented thus far have relied on plasticizers that, at best, form only hydrogen bonds with the gluten protein chains (see references above). The use of chemical crosslinkers to modify the properties of protein-based materials have been reported as well, but to induce crosslinking with the protein structure required either the use of a catalyst (Ghorpade, V. M. et al., *Trans ASAE* 1995, 38, 1805; Larré, C., *Agric. Food. Chem.* 2000, 48, 5444) or an aggressive radiation treatment (Brault. D., *Agric. Food. Chem.* 1997, 45, 2964).

Thus, much research has already been undertaken in order to obtain a gluten or zein based usable biodegradable polymer. However, all of these approaches encounter problems and a usable biodegradable polymer has not been described yet. For example, previously reported experiments, designed to improve the impact strength of the gluten material require the addition of at least 10-20% (w/w) of some plasticizer, such as glycerol or triethanolamine.

As a summary, there is still a great need for cost-effective biomaterials with adequate mechanical properties. Therefore, a goal of the present invention is to satisfy this need by developing a new biopolymer and biodegradable composite material with interesting properties such as an increased strength and toughness, by identifying a method for increasing the impact strength of natural proteins and fibers and by producing new biodegradable composite materials. This invention describes a method to improve the impact properties of gluten biopolymer, enabling broader usage of gluten in industrial applications. This invention also describes a new composite material and a process to make fully biodegradable composite materials.

Polythiols are molecules with multiple thiol groups in their structure and they are used for many reasons such as in the production of different polymers. The applications of these polymers include compositions for special coatings, inks and optical devices. Polythiols as crosslinking agents often influence the thermal and mechanical properties of the resulting polymers. In the prior art however, polythiols have not been used with natural polymers such as gluten.

SUMMARY OF THE INVENTION

The present invention relates to a new gluten polymer matrix, with tunable material properties and produced by using polythiol-containing molecules during the preparation process. The present invention also relates to the use of said gluten polymer matrix for industrial purposes. The present invention furthermore relates to a process or a method for preparing or forming said new polymer matrix and to the gluten polymer matrix produced through this process.

The present invention also relates to a new biodegradable composite material comprising gluten and fiber. The present invention furthermore relates to the use of said composite material for industrial applications and to a process or method for preparing said composite material.

The present invention thus relates to a new gluten polymer (matrix) prepared by using polythiol-containing molecules. The present invention relates to a new gluten polymer matrix prepared by using polythiol-containing molecules or comprising polythiol-containing molecules and having modified material properties. The invention relates to a new gluten polymer matrix comprising polythiol-containing molecules and with increased strain and strength, but with unaffected stiffness. The present invention relates furthermore to a new gluten polymer matrix wherein the gluten proteins are intermolecularly (and/or intramolecularly) covalently linked through a linker, more in particular through polythiol-containing molecules. The polythiol-containing molecules are crosslinking the gluten proteins. In a particular embodiment of the present invention, the gluten is wheat gluten.

In a particular embodiment of the invention, the polythiol-containing molecules are selected from the group consisting of 'TP200 3MP3', 'TP70 3MP3' or 'TMP 3MP3' or structural analogues thereof. Yet another particular embodiment relates to the use of polythiol-containing molecules, more in particular branched or hyperbranched polythiol-containing molecules, yet more in particular a tri-thiol containing molecule. The polythiol-containing molecules can be used to covalently crosslink the gluten proteins and/or to modify the gluten material properties. A particular polythiol-containing molecule is tri-thiol-containing polyol mercaptoester, such as "TP200 3MP3" (Perstorp Specialty Chemicals AB) (FIG. 1) or an active structural analogue thereof. In a particular embodiment of the invention, a mixture of different polythiol-containing molecules is used.

The present invention relates to a process for preparing the new gluten polymer matrix. The process comprises dispersing or mixing gluten in the presence of polythiol-containing molecules or combining gluten with polythiol-containing molecules in a gluten-dispersing mixture. In a certain embodiment, the process comprises the dispersion of gluten in the presence of at least 0.01% (w/w) of a polythiol-containing molecule versus gluten. In another embodiment of the present invention, the process comprises the dispersion of gluten in the presence of at least 0.01% (w/w) versus gluten or maximally 15% (w/w) versus gluten of a polythiol-containing molecule. In another embodiment at least 0.1% and maximally 1% of the polythiol-containing molecule is dipersed with gluten. In a particular embodiment of the invention the amount of polythiol-containing molecules used is directly proportional to the amount of cysteine in the gluten. In a particular embodiment of the invention, the polythiol-containing molecule is used in stoichiometrical amounts relative to the cysteines in gluten in order to have as many moles thiol from the polythiol-containing molecules as moles thiol from the cysteines in gluten. In a particular embodiment of the invention the amounts of gluten and polythiol-containing molecules used is such that there are approximately as many mole thiols from gluten as moles thiol from the polythiol-containing molecules in the mixture.

In a certain embodiment of the invention, the gluten can be dispersed, mixed or combined in a gluten-dispersing mixture. The gluten can be dispersed in aqueous environments such as alcohol-water mixtures or alkaline or acidic conditions, or non-aqueous environments such as pure methanol or ethanol, by using aiding agents such as hydrogen bond breakers, chaotropic agents and detergents and by using other solvents such as ketones or amide solvents or mixtures thereof. In a particular embodiment the gluten is dispersed under mild acidic conditions, more particularly in an acetic acid solution, yet more in particular in dilute acetic acid and still more in particular in 0.05 M acetic acid or the gluten in dispersed under mild alkali conditions. In another particular embodiment the gluten is dispersed in an alcohol-water mixture, more in particular in 50% (v/v) propanol-water solution or in 70% (v/v) ethanol-water solution.

In another embodiment of the invention, the process for the preparation of the new gluten polymer also comprises an isolation step. In a certain embodiment the isolation step consists of precipitating the proteins or a fraction thereof, for example by changing the pH of the dispersion, by changing the concentration of one of the solvents used or by changing the ionic strength of the mixture. In a particular embodiment of the invention, the precipitation is obtained by increasing the pH from acid conditions, more in particular mild acid conditions (pH 3-4) to a neutral pH (6-8) or even higher, more in particular by using NaOH, more particularly dilute NaOH. In another embodiment the isolation step comprises the precipitation of the proteins and subsequent centrifugation.

In a further embodiment of present invention a precipitate of gluten modified by the polythiol-containing molecule, in particular by a tri-thiol-containing polyol mercaptoester and more in particular by the TP200 3MP3, can be formed by increasing the pH of the mixture from acid conditions to a higher pH until the precipitation occurs, a fraction of the proteins has precipitated or the precipitation is complete (neutral or alkaline conditions), more in particular by changing the pH from 3-5 to 6-8.

Alternatively a method can be used wherein an alcohol-based aqueous solution is used, particularly a 50% (v/v) propanol solution for dispersing the gluten together with the polythiol-containing molecule and that the precipitation is obtained by adding more propanol.

Yet another embodiment of the process comprises the drying of the dispersion or the precipitate, centrifugated or not, by for example drying on the air, drying with hot air, spray-drying or freeze-drying with or without a precipitation step or centrifugation.

In yet another particular embodiment, the process for the preparation of the new gluten matrix also comprises a compression-molding (and/or thermo-molding) step, thereby applying pressure and a temperature raise. The new matrix can be placed in a mold and processed at a variety of different pressures and temperatures. The compression molding-step consists of compression-molding the protein for several minutes, ranging from 1 to 20 minutes, more in particular from 5 to 15 minutes and yet more in particular for 10 minutes. In a certain embodiment of the process the compression-molding is performed at a minimum temperature of 100° C. and a minimum pressure of 2 bars for minimum 1 minute. In another embodiment the compression-molding step is performed at 150° C./5 bars or 25 bars for 10 minutes. In another particular embodiment the process comprises a subsequent cooling, more in particular to a temperature below 40° C., more in particular below 30° C. over a time period between minimum 1 minute and maximum 20 minutes. An object of this embodiment relates to cooling below 40° C. over a period of at least 15 minutes and yet more in particular to a temperature below 20° C. over a period of 5 minutes.

In a very particular embodiment of the present invention, there is a time period between the dispersing of the gluten in the gluten-dispersing mixture together with the polythiol-containing molecules, the precipitation and centrifugation and/or evaporation and the drying at one side and the compression-molding at the other side. In this particular embodiment there is a time period that the dried materials can not be handled before the compression molding step. This time period that the dried material is left unhandled before compression-molding is at least one week (7 days) or at least 30 days or 60 days or 90 days or between 30 days and maximally 180 days. The temperature for on which the material is aged is in a particular embodiment room temperature. In another embodiment this temperature is however under 25° C. or higher than 25° C., more particularly higher than 40° C.

The present invention furthermore relates to a process for preparing a new gluten biopolymer with modulated mechanical properties, more in particular with modulated strength and strain and/or stiffness, and yet more in particular with an increased strength and strain and unmodulated stiffness.

The present invention also relates to a process for improving the impact properties of gluten biopolymer with the inclusion of low levels of a polythiol-containing molecule into the gluten biopolymer dispersion.

The present invention furthermore relates to a method for preparing or forming a biodegradable article or a new gluten based polymer comprising the steps of dispersing and mixing the gluten in a polythiol-containing molecule containing gluten-dispersing mixture, precipitating the reaction products out of the medium, centrifuging the mixture, drying the precipitate, leaving the dried material unhandled for a certain time period and compression-molding the precipitate or a selection or combination hereof. The present invention also relates to a method for preparing a new gluten based polymer comprising the steps of dispersing and mixing the gluten in a polythiol-containing molecule containing gluten-dispersing mixture, drying the mixture, leaving the dried material unhandled for a certain time period and compression-molding the dried mixture or a selection or combination hereof.

In a particular embodiment of the present invention, the strength of the gluten polymer is at least 25 Mpa and more particularly at least 30 Mpa, while the strain is at least 0.04, more particularly 0.05, while the stiffness is between 500 and 1500 MPa or not higher than 1500 MPa or nor lower than 500 MPa.

The present invention also relates to a new composite material containing fiber, characterised in that the fiber is coated with gluten. The new composite material therefore comprises fiber on which gluten is adhered. In a particular embodiment of the invention, the fibers used in the composite material are selected from synthetic fibers, wooden fibers, nonwood fibers, natural fibers, biodegradable fibers or other fibers comprising cellulose, lignin and/or pentosans. In a more particular embodiment, the fiber is flax fiber or glass fiber. In a particular embodiment, the fibers used in the invention are long fibers.

The present invention also relates to a process or method for preparing said new composite materials. The present invention furthermore relates to a process for preparing the gluten-coated fiber, comprising the steps of pre-coating the fiber with gluten (under dry circumstances), than contacting the pre-coated fiber with a gluten-dispersing mixture (e.g. aqueous medium or non-aqueous medium which has the capacity to disperse gluten), more particularly with a neutral (pH around 7) aqueous medium and drying the resulting material, followed or not with a compression-molding step. The invention also relates to a process for preparing the gluten-coated fiber, comprising the steps of placing the fiber (not pre-coated) together with the gluten, with or without polythiol containing molecules, in an aqueous medium or non-aqueous medium which has the capacity to disperse gluten, more particularly in a neutral (pH around 7) aqueous medium and drying the resulting material. The gluten used in the preparation of gluten-coated fibers can be unmodified commercial gluten, gluten derivatives or fractions or modified gluten prepared by applying polythiol-containing molecules with the process described above in dry state or wet state.

In a particular embodiment of the process for preparing the gluten coated fiber, the pre-coating of the fiber can be performed by contacting the fiber with gluten or by bringing the gluten powder onto the fiber, by sprinkling, by using the "fluidized bed" technology, by applying pressure, or by any known method in the art. In another embodiment of the process for preparing the gluten coated fiber, the gluten pre-coated fiber is contacted with or placed in a gluten-dispersing mixture like water (acidic, alkaline or neutral), more in particular water with a pH around 7, for some time, more in particular for several seconds to minutes.

Alternatively, the present invention relates to a process for preparing gluten-coated fiber, comprising mixing a fiber in a dispersion of gluten, precipitating the gluten onto the fiber and drying the resulting material. In a particular embodiment of this process, the fibers are mixed in a dispersion of gluten, with or without polythiol-containing molecules. In the case the fibers are dispersed with gluten without polythiol-containing molecules, the gluten used can already have been modified by polythiol-containing molecuels by the processes described above. In a certain embodiment of the invention, the gluten can be dispersed as described above in a gluten-dispersing mixture, under alkaline or acidic conditions or other aqueous environments such as alcohol-water mixtures, in non-aqueous environments such as pure methanol or ethanol, by using aiding agents such as hydrogen bond breakers, chaotropic agents and detergents and by using other solvents such as ketones or amide solvents. In a particular embodiment the gluten is dispersed under mild acidic conditions, more particularly in an acetic acid solution, yet more in particular in 0.05 M acetic acid. In another particular embodiment the gluten is dispersed in a alcohol-water mixture, more in particular in a 50% (v/v) propanol-water solution. Following, the gluten can be precipitated onto the fibers or the solvents can be evaporated from the mixture. In a particular embodiment of the process, the gluten is precipitated by changing the pH to approximately neutral or by changing the concentration of the solvents. Yet another embodiment of the process comprises the drying of the dispersion, by for example drying on the air, spray-drying or freeze-drying with or without a precipitation step or centrifugation.

In another particular embodiment, the above mentioned steps can be followed by a time period that the material is left unhandled and a compression-molding step as described above.

A further embodiment of present invention is a process to form a cohesive gluten polymer network around fibers. Fibers are covered by gluten powder (in certain embodiments 1/1 w/w) and consequently contacted for a certain period (for instance 30 second) with a gluten-dispersing mixture like water (acidic, alkaline or neutral), more in particular deionised water, more in particular in water with a pH around 7 or water with base, particularly NaOH or by contacting said gluten powder covered fibers with alkaline water, preferably deioinsed water with a pH of at least 8 or higher for instance by dipping said mixture of said fibers and said gluten powder for less than one minute in said water. FIG. 4 demonstrates gluten coated fibers obtained by immersing fibers with gluten powder in alkaline water for less than a minute. The fibers can be synthetic fibers (e.g. polypropylene fibers or polyethylene fibers) wooden fibers or nonwood fibers (e.g. flax fibers), a combination of wood and nonwood fibers, natural fibers, biodegradable fibers or other fibers comprising cellulose, lignin and/or pentosans. The wood fibers or nonwood fibers can be unmodified natural fibers or can be chemically modified. The gluten biopolymer stays on the fibers even after the gluten-fiber mixture is dried (FIG. 5).

An alternative approach of gluten coating of fibers is to immerse natural wood or nonwood fibers in a gluten dispersion (as described above), in particularly in an aqueous environment, such as dilute acid, dilute alkali or dilute alcohol gluten solution. The soluble gluten molecules are allowed to interpenetrate the swelling fibers. Optionally polythiol-containing molecules can be added above 0.5% (w/w), about 0.5% (w/w), from 0.5% to 0.1% (w/w), less than 0.1% (w/w), above 0.1% (w/w), above 1% (w/w) and not more than 6% (w/w). By changing the pH, mixing other solvents like ethanol or solvent evaporation a strong adhesive bound is formed between the natural fibers and the gluten.

In yet another particular embodiment, the process for the preparation of the new gluten coated fiber matrix also comprises a compression-molding or thermo-molding step as described above. This fiber/gluten matrix can be compression-molded, for instance for 10 minutes at 150° C. at a pressure of between 2 and 200 bars and cooled to form a fiber reinforced gluten polymer article.

The new gluten polymer matrix of the present invention is optionally prepared without the use of a plasticizer, besides the polythiol-containing molecules and/or water used in the process. The process for preparing a gluten polymer comprising the step of mixing the gluten in an aqueous environment with polythiol-containing molecules, optionally excludes the use of a plasticizer besides the polythiol-containing molecules and/or water used in the process. This process furthermore optionally excludes the heating of the mixture of the gluten and the polythiol-containing molecules in an aqueous environment before the compression molding step. In another particular embodiment, the process of the invention could also be performed with thiol-containing molecules, more in particular the process involving pre-coating fibers with gluten.

The present invention furthermore relates to the industrial use of the above described biodegradable materials. The materials can for example be used in the automotive, food or medical industry as materials for the construction of cars, as packaging material or as material for the construction of medical devices respectively. Solid, non-edible biodegradable gluten based articles have a wide area of applications and industrial use. Biodegradable products (in a relatively short period destructible) or polymers can be used in eating utensils, cups, plates, sheet items, packaging and other convenience products, presently mostly fabricated by indestructible polymers.

BRIEF DESCRIPTION OF THE FIGURES

FIG. 8. SE-HPLC data for different samples in order to evaluate the influence of thiol-modification and molding.
a. SE-HPLC data for several unreduced samples (thiol-modified or not and molded or not)
b. SE-HPLC data for the same samples as in FIG. 8a but after treatment with dithiotreitol (DTT).

The figure indicates that molded samples contain less monomers and more SDS-unextractable polymers than unmolded samples. This suggests more extensive crosslinking of the polymers and incorporation of gliadins into the polymers as a result of the molding process (pressure and temperature raise). The figure also shows that incubation with a thiol-containing molecule results in lower size polymers and a higher level of monomers before molding suggesting that the thiol-containing molecule acts as a reducing agent and breaks disulfide bridges. After molding, however, samples with the thiol-containing molecule had even lower levels of monomers and higher levels of SDS-unextractable polymers than molded samples without the thiol-containing molecule suggesting even more extensive cross-linking as a result of the presence of the thiol-containing molecule.

Figure 9A:
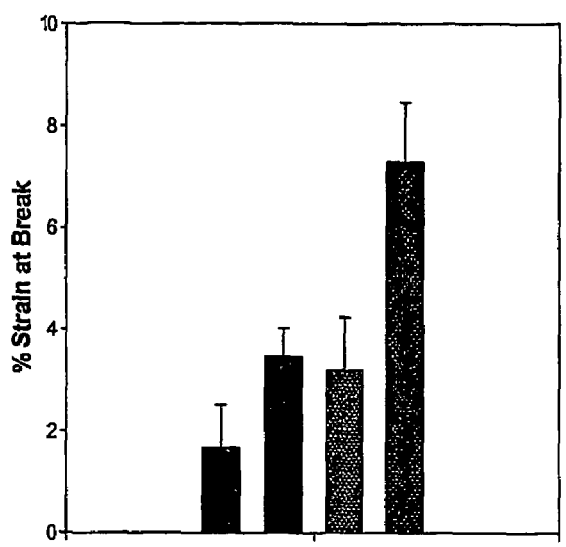
Figure 9B:
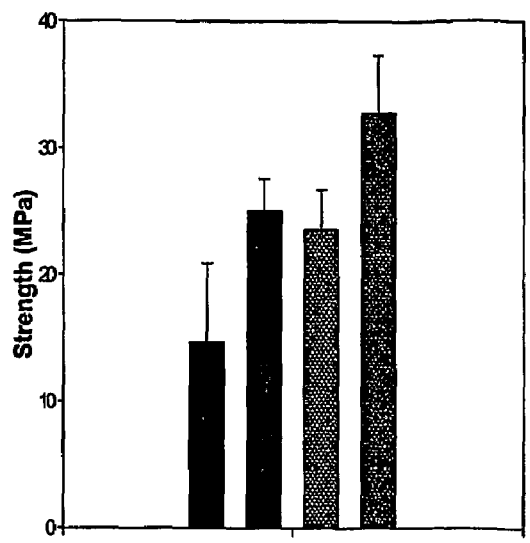

FIG. 9. Mechanical properties of molded gluten specimens (as used in FIG. 10): Strain-to-failure and strength.
a. Mean values of % strain at break illustrating increase in strain-to-failure as the gluten formulations aged with time. The first and the third bars from the left depict specimens molded from unmodified powder, while the second and fourth bars represent specimens molded from tri-thiol-modified gluten powder. The two last bars from the left represent samples molded and tested long after preparation of the dry material (in July), while the two first bars from the left illustrate specimens that were molded and tested three months before (in april of the same year), namely shortly after the preparation of the dry material. The error bars are equivalent to one standard deviation.
b. Mean values of strength illustrating a similar increase in strength as the gluten formulations aged with time (the samples were left unhandled for a period of time before molding).

Figure 10:
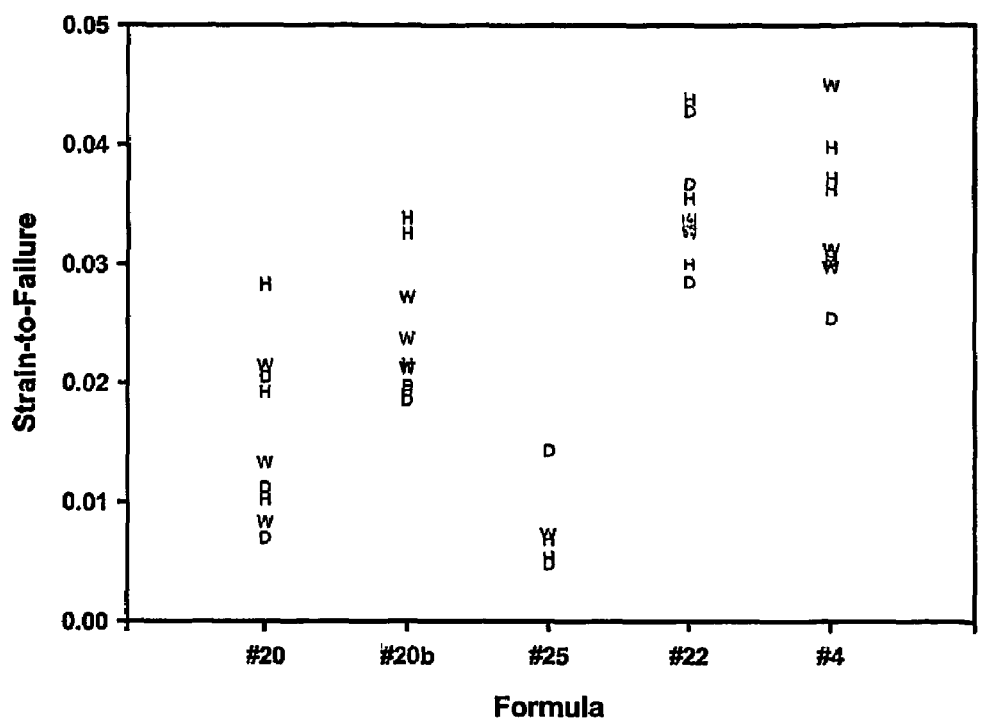
Figure 10:
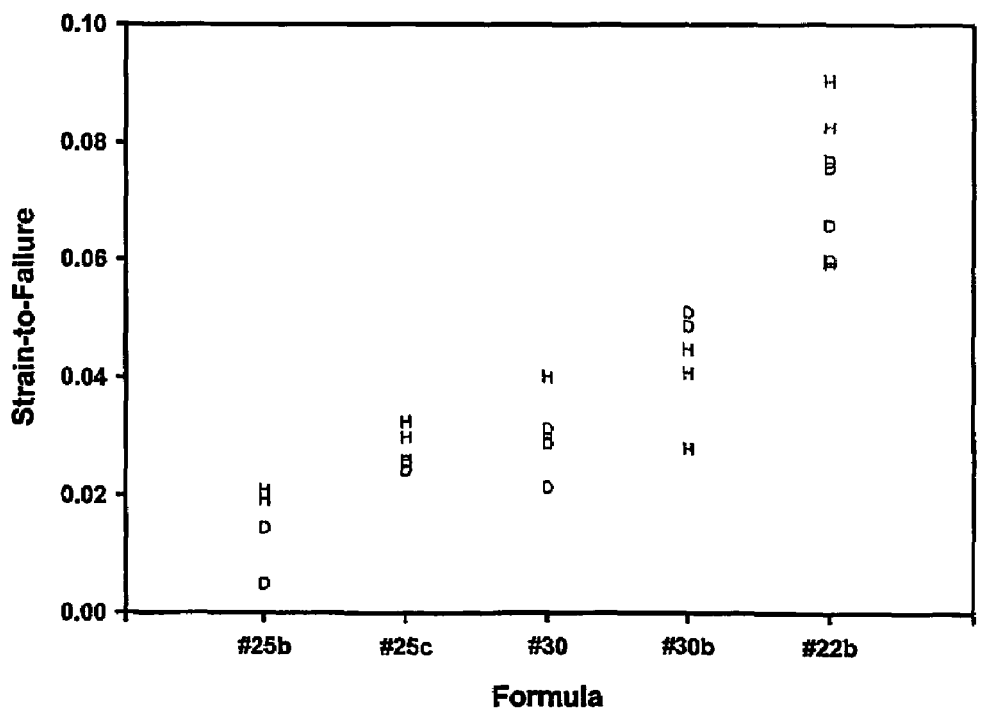
Figure 10C:
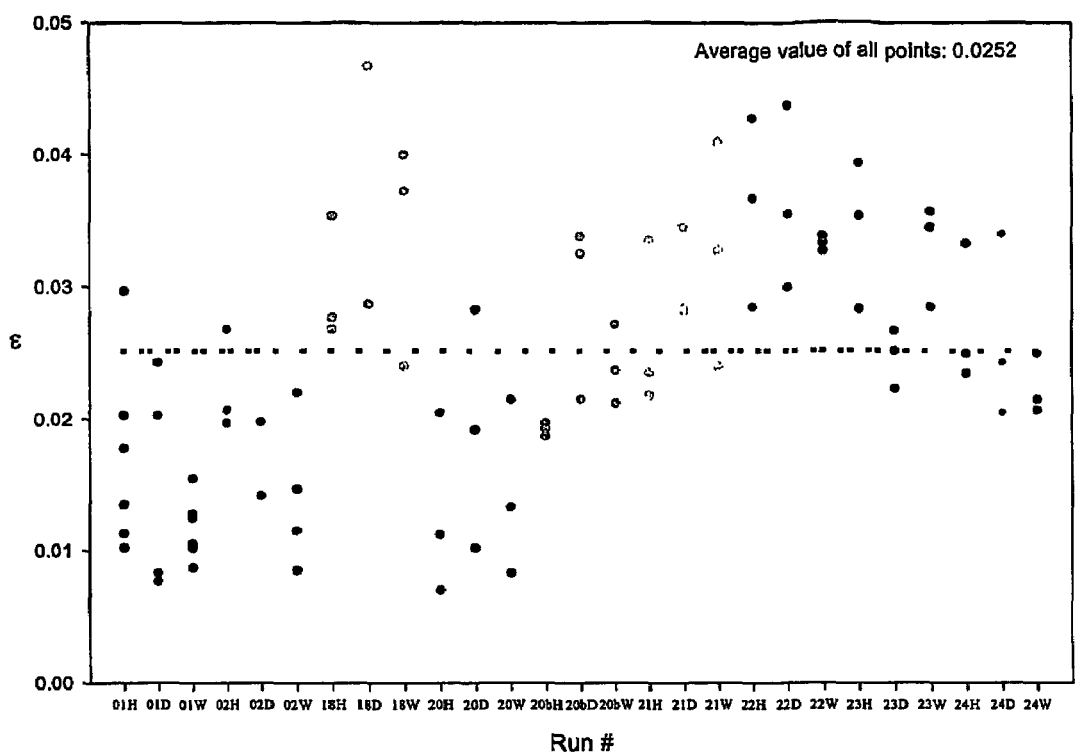
Figure 10D:
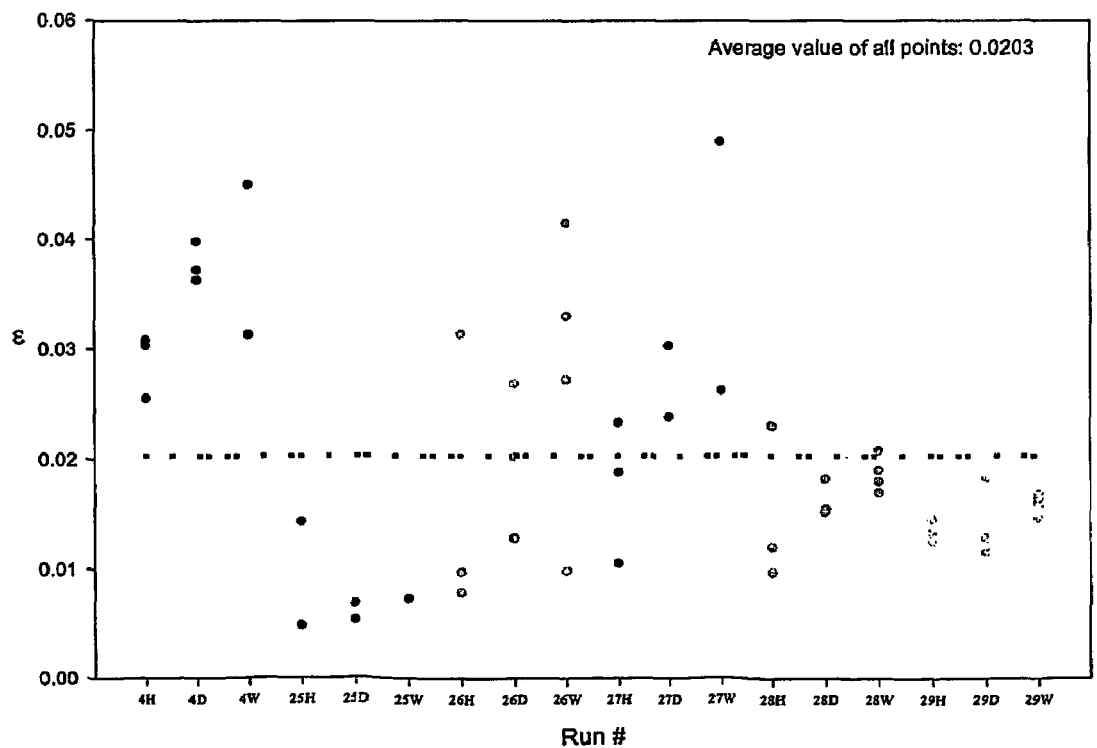

FIG. 10. Mechanical properties of molded gluten specimens: Strain-to-failure
a. Samples 20, 20b and 25 are native gluten, while samples 22 and 4 were made using stoichiometric amounts of thiol with respect to the cysteines in gluten. Specimens were molded in April, shortly after they were prepared.
b. Samples 25b, 25c, 30 and 30b are native gluten, while sample 22b was made using stoichiometric amounts of thiol with respect to the cysteines in gluten. Specimens were molded 3 months later than the samples of FIG. 10a.
c-d. Additional data illustrating changes in mechanical properties due to the addition of fiber (#18) or different thiol-containing molecules in different amounts [cysteine (#21, #26), DTT (#27), TP70 3MP3 (#2, #23) and TP200 3MP3 (#22, #4, #28)].

25b, 25c, etc. in the figure indicate a second or third molding from the same preparations. H, D, and W indicate measurements acquired one hour, one day or one week after molding.

Figure 11:
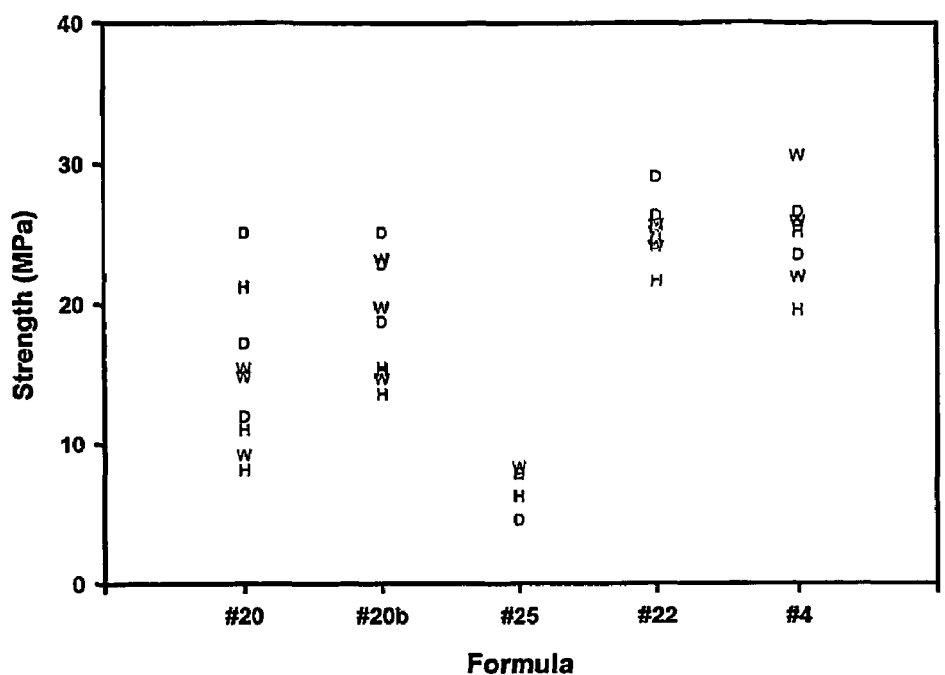
Figure 11:
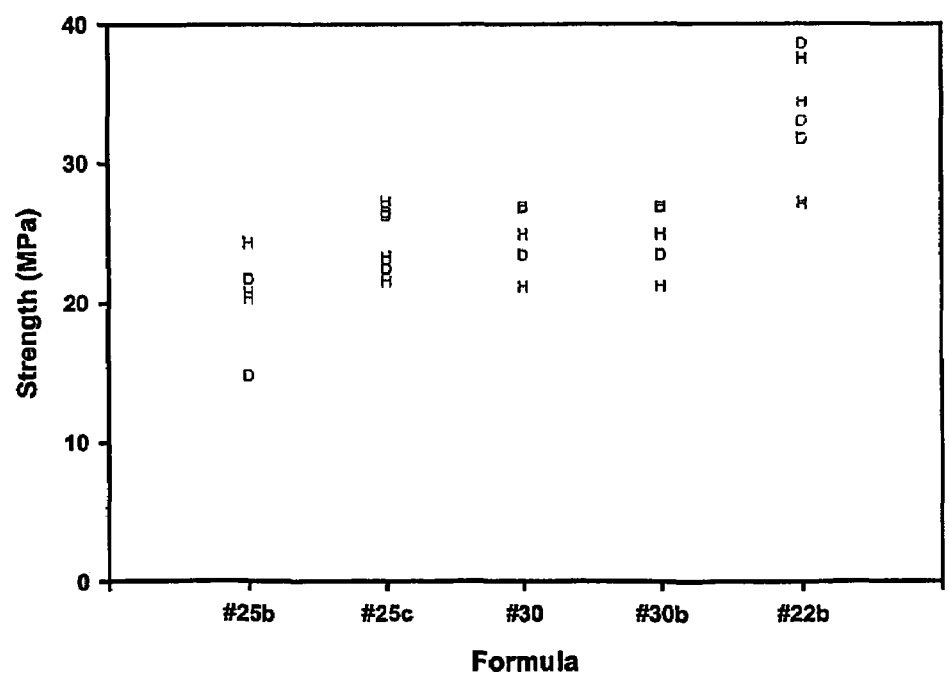
Figure 11C:
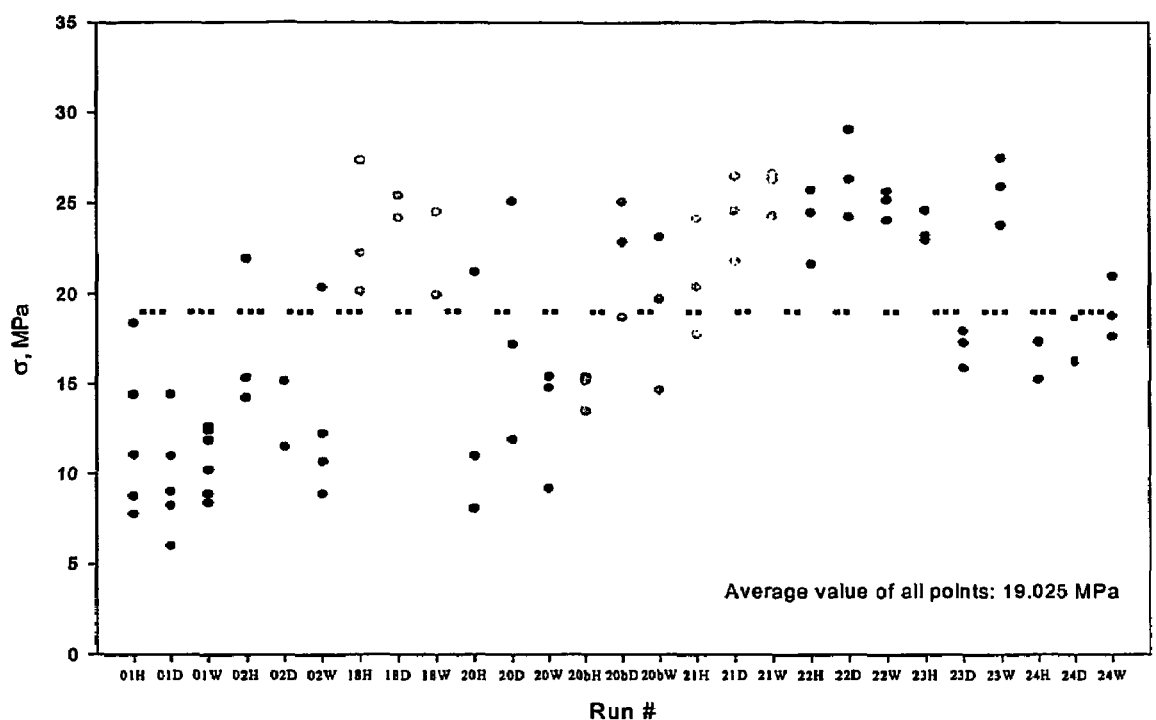
Figure 11D:
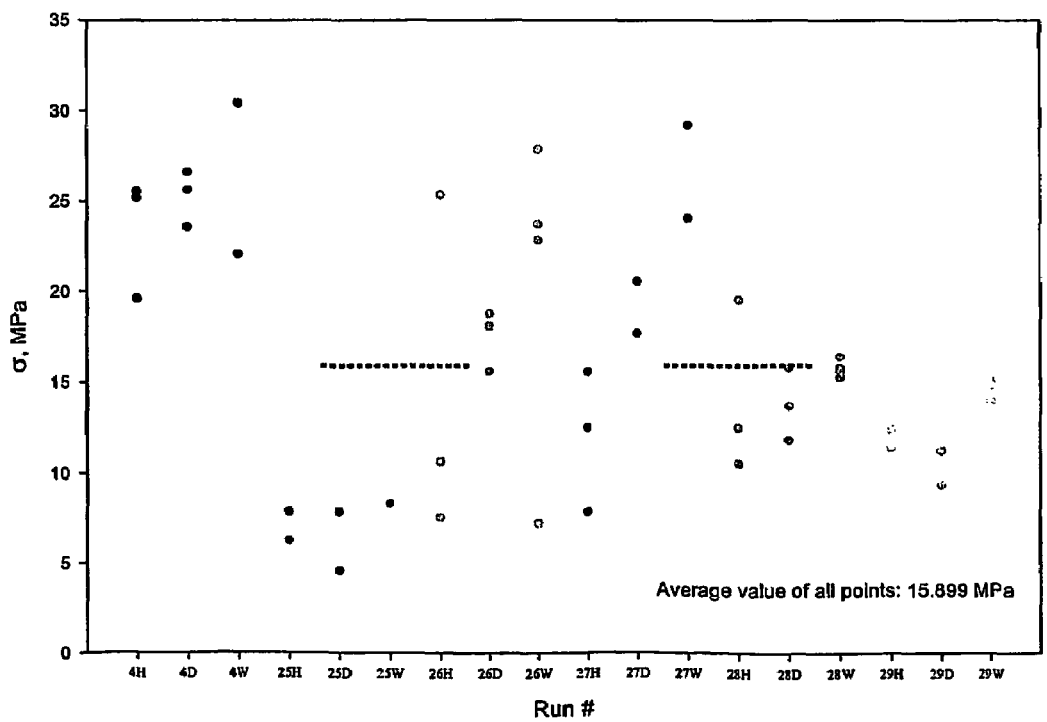

FIG. 11. Mechanical properties of molded gluten specimens: Strength For the same samples and under the same conditions as in FIG. 10.

Figure 12:
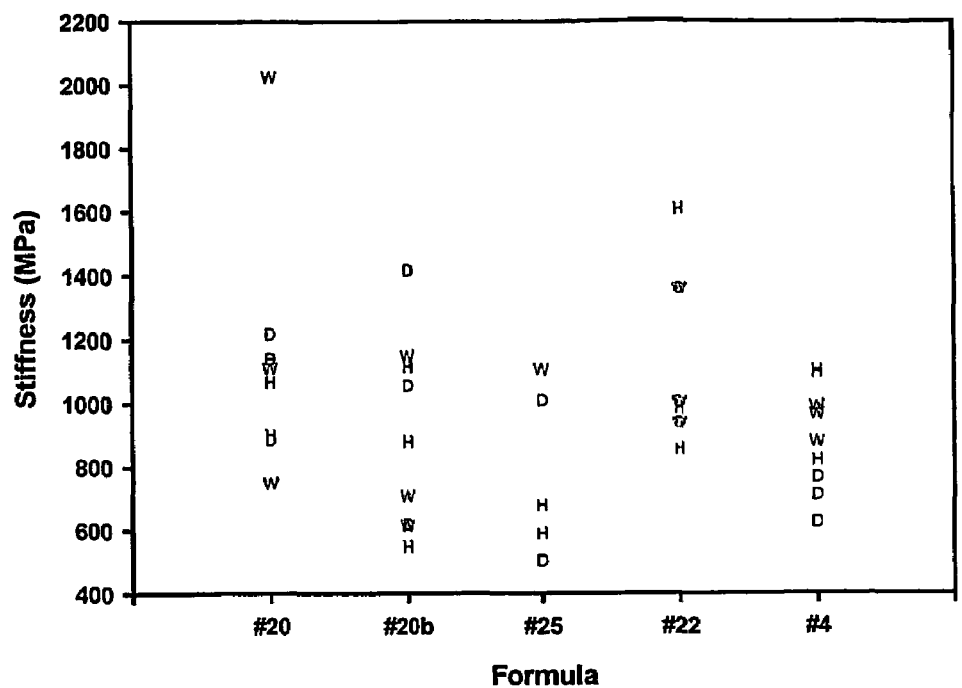
Figure 12:
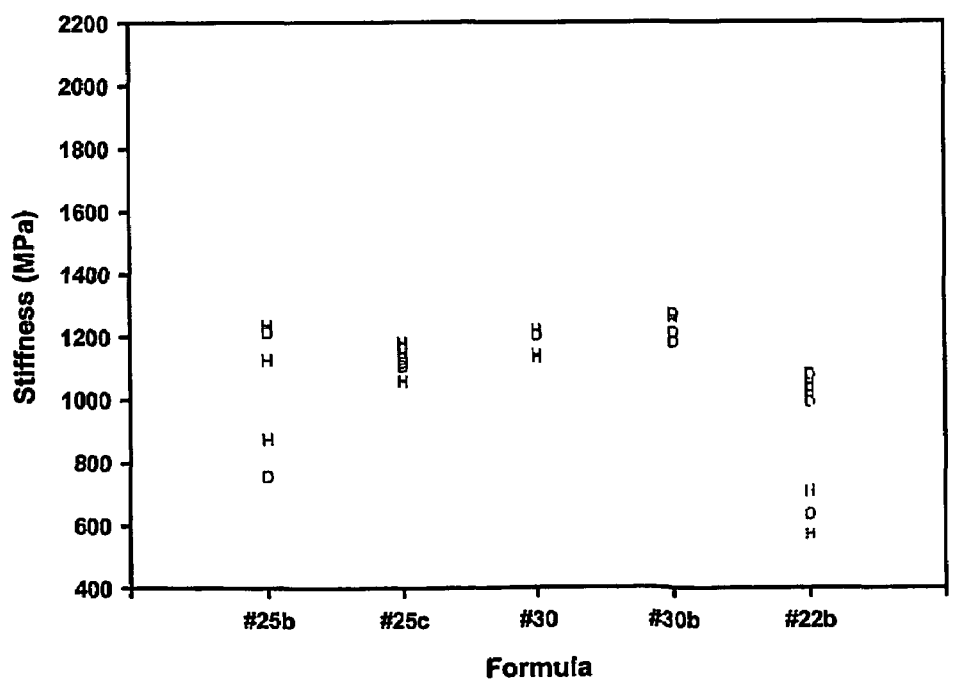
Figure 12C:
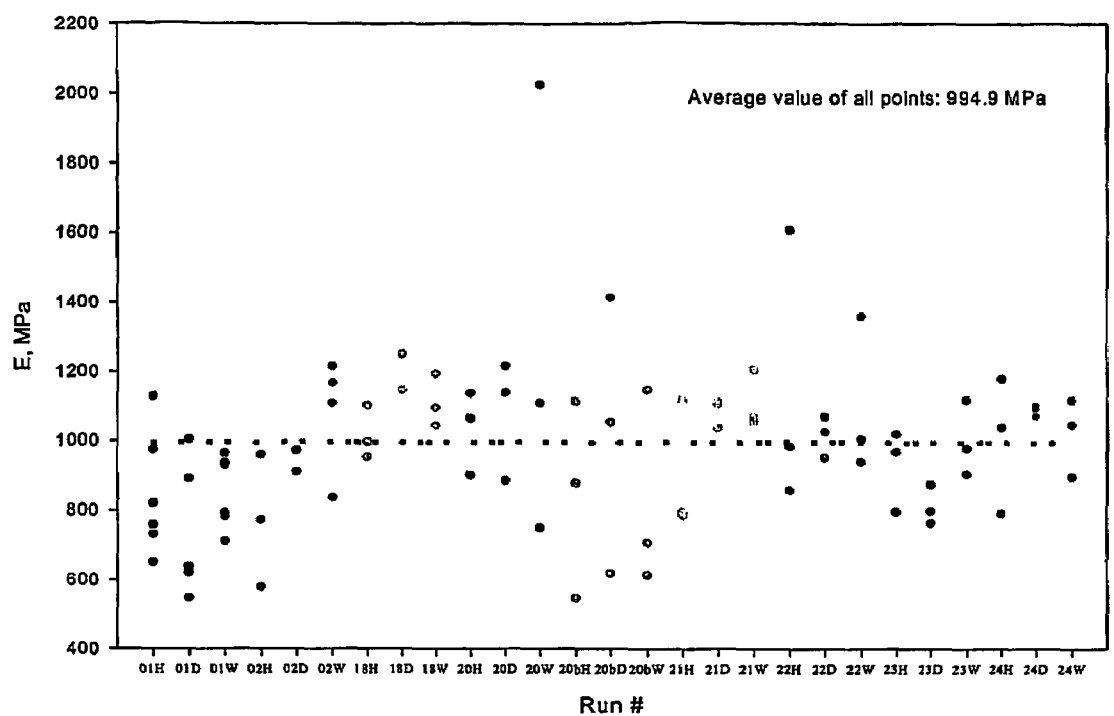
Figure 12D:
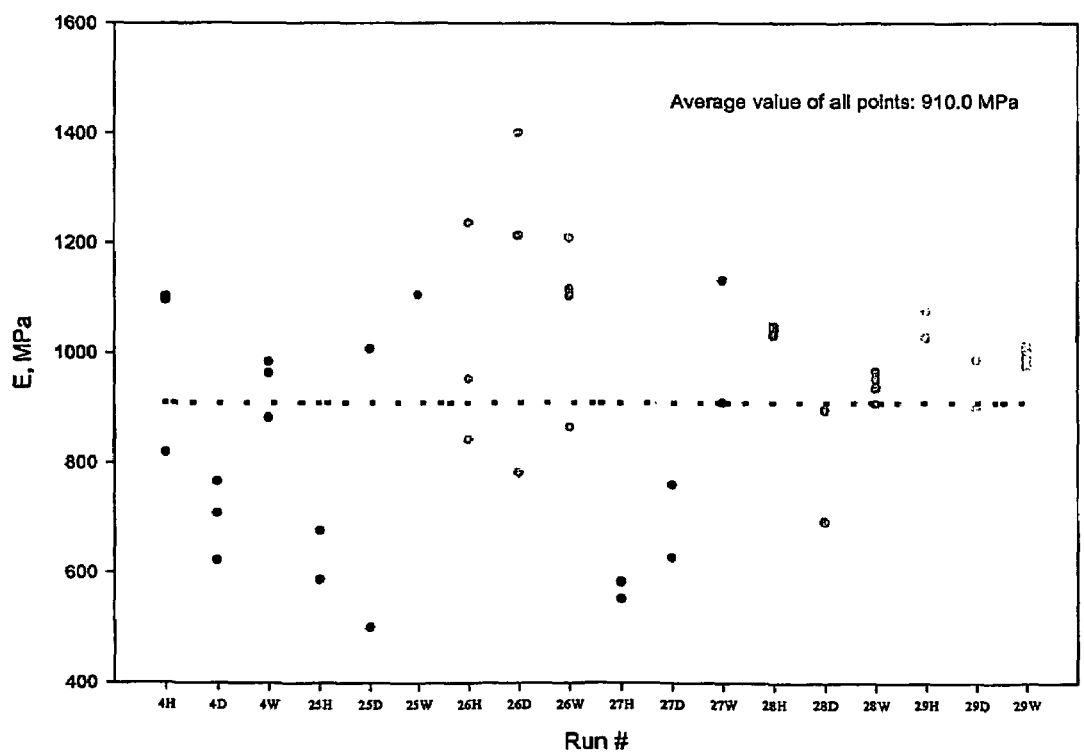

FIG. 12. Mechanical properties of molded gluten specimens: Stiffness For the same samples and under the same conditions as in FIG. 10.

FIG. 13. Picture of mold without and with a gluten sample.

DETAILED DESCRIPTION OF THE INVENTION

The terminology used herein is for the purpose of describing particular embodiments only, and is not intended to limit the scope of the present invention.

Definitions

As used in the specification and the appended claims, the terms "fibers" and "fibrous materials" include both inorganic fibers or fabric and organic fibers and fabric. In general, fibers can be classified into three categories: wood, nonwood, and nonplant.

Fibers that may be incorporated into gluten matrix preferably include naturally occurring organic fibers, such as cellulosic fibers extracted from hemp, cotton, plant leaves, sisal, abaca, bagasse, wood (both hardwood or softwood, examples of which include southern hardwood and southern pine, respectively), or stems, husks, shells, and fruits or any nonwood fiber as defined hereunder, or inorganic fibers made from glass, graphite, silica, ceramic, or metal materials. Any equivalent fiber which imparts strength and flexibility is also within the scope of the present invention.

The term "nonwood fibers" as used herein is thus to distinguish plant fibers from wood fibers (softwood or hardwood), the fibers can be derived from selected tissues of various mono- or dicotyledonous plants. And are categorized botanically as grass, bast, leaf, or fruit fibers. The nonwood fibers can also be classified by means of production such as sugar cane bagasse, wheat, straw and corn stalks byproducts. They can also be grouped as "fiber plants", plants with high cellulose content that are cultivated primarily for the sake of their fibers such as jute, kenaf, flax, cotton and ramie. An example of nonwood fibers are fibers consisting of the group of Jute, flax, cotton, Hemp, Kenaf, Pina, Abaca, Sisal, Hennequen, Stalk (Rice, Wheat, Barley, Oat, Rye), Cane (Sugar, Bamboo), Grass (Esparto, Sobai), Reed (e.g. Phragnites communis), Bast (Seed flax, Kenaf, Jute, Hemp, Ramie), core (Kenaf, Jute), Leaf (Abaca (e.g. Manila), Sisal (e.g. Agave)), Seed hull (e.g. cotton linter).

In a particular embodiment the fibers used are long fibers (longer than 2 to 3 cm) or optionally short fibers are excluded.

The term "polythiol-containing molecule(s)" as used herein refers to molecules with at least two free thiol groups. In particular embodiments the polythiol-containing molecules have at least three free thiol groups, particularly thiol groups that have a free electron pair and in a particular case have reducing capacity. The molecules can be straight, branched or hyperbranched. In a particular case, the polythiol-containing molecules have thiol groups that are separated from each other so that they can not easily react intramolecularly. Examples of polythiol-containing molecules are 'TP200 3MP3', 'TP70 3MP3' or 'TMP 3MP3' (Trimethylolpropane Tri(3-mercaptopropionate)) (Perstorp Speciality Chemicals, Aldrich Chemicals), the three last ones differing with respect to their degree of ethoxylation (the first carries twenty ethylene oxide units, the second carries seven, and the last does not carry any ethylene oxide units at all). 'TP200 3MP3' has a high flexibility and water compatibility. Other examples are dithiotreitol, Glycol Dimercaptoacetate, Glycol Dithioglycolate, Glycol Di(3-mercaptopropionate), Pentaerythritol, Tetramercaptoacetate, Pentaerythritol Tetrathioglycolate, Pentaerythritol Tetra(3-mercaptopropionate, Trimethylolpropane Trimercaptoacetate, Trimethylolpropane Trithioglycolate, Trimethylolpropane Tri(3-mercaptopropionate), Trimethylolethane Trimercaptoacetate, Trimethylolethane Trithioglycolate, Trimethylolethane Tri(3-mercaptopropionate, Di-Trimethylolpropane Tetramercaptoacetate. Other polythiol-containing molecules can be synthesized by esterification of a polyol such as glycol, pentaerythritol, trimethylolpropane, trimetyloletrane or di-trimethylolpropane with for example mercaptocarboxylic acids such as mercaptobutyric acid. The synthesis of polythiol-containing molecules out of polyols is also described in the prior art. In a particular embodiment of the invention, peptides or proteins containing multiple cysteines could also serve as polythiol-containing molecules. The term polythiol-containing molecules optionally excludes thiol redox proteins such as thioredoxin or glutaredoxin.

The term "thiol-containing molecules" refers to molecules with at least one free thiol group.

The term "gluten" as used herein refers to the commercially available wheat gluten from for example Amylum (Aalst, Belgium). The term gluten however also refers to gluten as a composition containing gliadins and glutenins in different amounts. It is however clear to a person skilled in the art that gluten as used in this invention can also mean any composition containing at least 20% storage proteins derived from a plant, or more particularly from a seed (e.g. soy) or a cereal, yet more particularly from a prolamine rich cereal (wheat, maize, barley, sorghum, millets, rye) or in particular from wheat, maize, rice, barley, sorghum, millets, rye or oats. The term can also refer to fractions of al the above described compositions and derivatives or modified gluten (chemically or enzymatically).

It is also clear to a person skilled in the art that "gluten" could also refer to a synthetic mixture which is analogous to the gluten obtained from naturally occurring plants.

The term "gluten-dispersing mixture" refers to any mixture comprising at least one liquid or solvent that is able to at least disperse gluten. The gluten dispersing mixture refers also to mixtures able to solubilize or dissolve gluten. Gluten can be dispersed in aqueous environments such as alcohol-water mixtures in different percentages. Gluten can also be dispersed under aqueous alkaline or acidic conditions or non-aqueous environments such as pure methanol or ethanol, by using aiding agents such as hydrogen bond breakers, chaotropic agents and detergents and by using other solvents such as ketones or amide solvents or mixtures thereof. Examples of gluten dispersing mixtures are mild acidic conditions like a (dilute) acetic acid solution, mild alkali conditions, alcohol-water mixture of 50% (v/v) propanol or 70% (v/v) ethanol, and some gluten is dispersable in pure methanol.

Description

The present invention shows that gluten can be formed into a tough plastic like substance with interesting properties by using thiol-containing molecules during its preparation. This led to the possibility of developing biodegradable high performance engineering plastics and composites from renewable resources that are far less expensive than their synthetic counterparts. The present invention showed that an otherwise brittle protein-based material can be toughened by increasing the yield stress and strain to failure, without compromising stiffness.

In the present work, the fracture toughness of the gluten polymer was improved by a factor of ten or more with the addition of a polythiol-containing molecule such as a tri-thiol-containing modifying agent and by applying the rest of the process of the invention (i.e. aging). The polythiol-containing molecules have another notable attribute, namely, that under proper chemical and environmental conditions, they have the potential to bond chemically with the gluten biopolymer via sulfhydryl/disulfide exchange reactions, giving rise to a potentially more stable material (e.g. a stabilized gluten foam). In addition, the process does not require the addition of other agents, such as plasticizing agents or salts. The water absorption data (FIG. 7) show to the fact that the polythiol-containing molecules are cross-linked with the gluten proteins.

The amount of polythiol-containing molecules used in the process can be calculated in regard of the amount of cysteines (free and involved in disulfide bonds) in the gluten. The amount of cysteines in a protein or in gluten can easily be determined by applying methods known in the art like the automated Edman degradation procedure using phenyl isothiocyanate (PITC) or the acid hydrolysis combined with ion-exchange chromatography and detection with the use of ninhydrin. The amount of cysteines in gluten can also be found in literature and is around 13.82 mmole cysteines per 100 g gluten. The amount of thiol groups in a molecule can easily be calculated, so that for example the polythiol-containing molecule TP200 3MP3 contains 2.35 mmol SH per g molecule. Starting from these data the amounts used of gluten and polythiol-containing molecules can be calculated to have stoeichiometrical amounts. 5.8% (w/w) TP200 3MP3 corresponds therefore stoichiometrically to the amount of thiol groups in gluten. The same for 3.2% (w/w) of TP70 3MP3, 1% (w/w) of DTT and 1.7% (w/w) of cysteine.

The present invention relates to the incorporation of polythiol-containing molecules, for instance TP200 3MP3 from Perstorp Specialty Chemicals AB, into the gluten biopolymer and to the crosslinking of the polythiol-conating molecules with the gluten network, giving rise to a tougher material system. Inherent challenges in processing gluten are attributed to the low solubility of gluten in most solvents, as well as its high melt viscosity.

Figure 1:
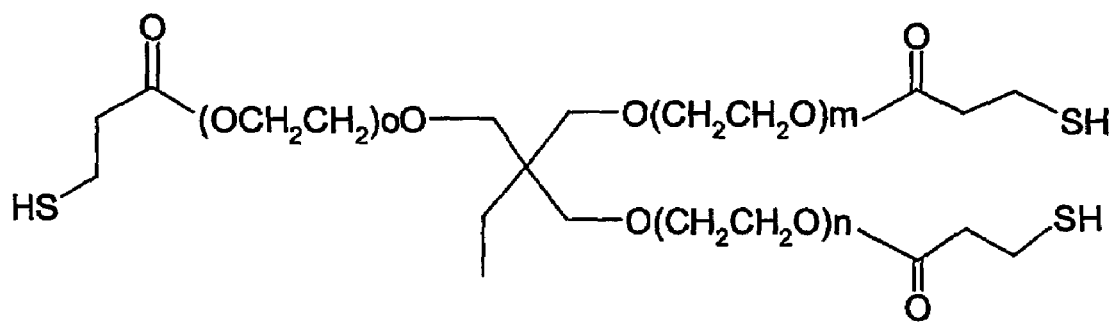
FIG. 1. Schematic of the polyol mercaptoester, TP200 3MP3, m+n+o=20.
Figure 2:
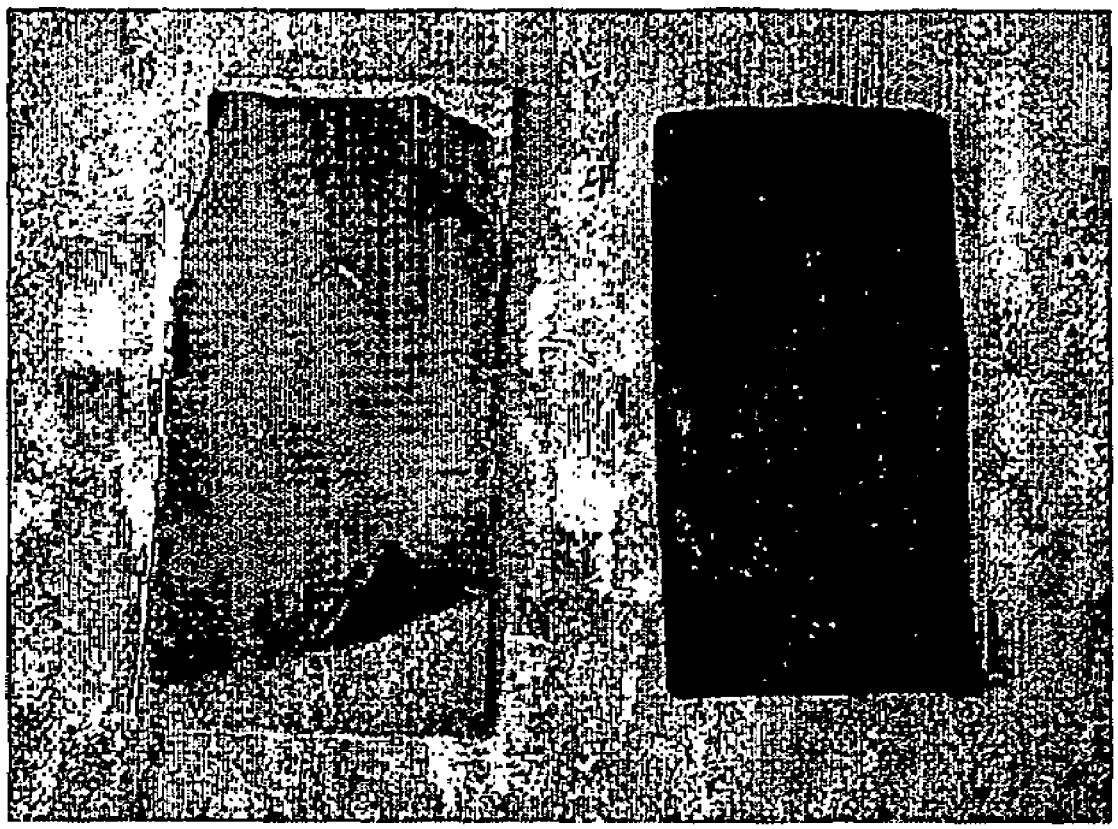
FIG. 2. Photograph of an unmodified gluten specimen (left) and TP200 3MP3-modified-gluten specimen (right) obtained by the methods described. These materials were compression-molded for 10 minutes at 150° C. at a pressure of 25 bars. The temperature of the press was subsequently decreased to 20° C. before the mold was removed from the press and the parts demolded.
Figure 3:
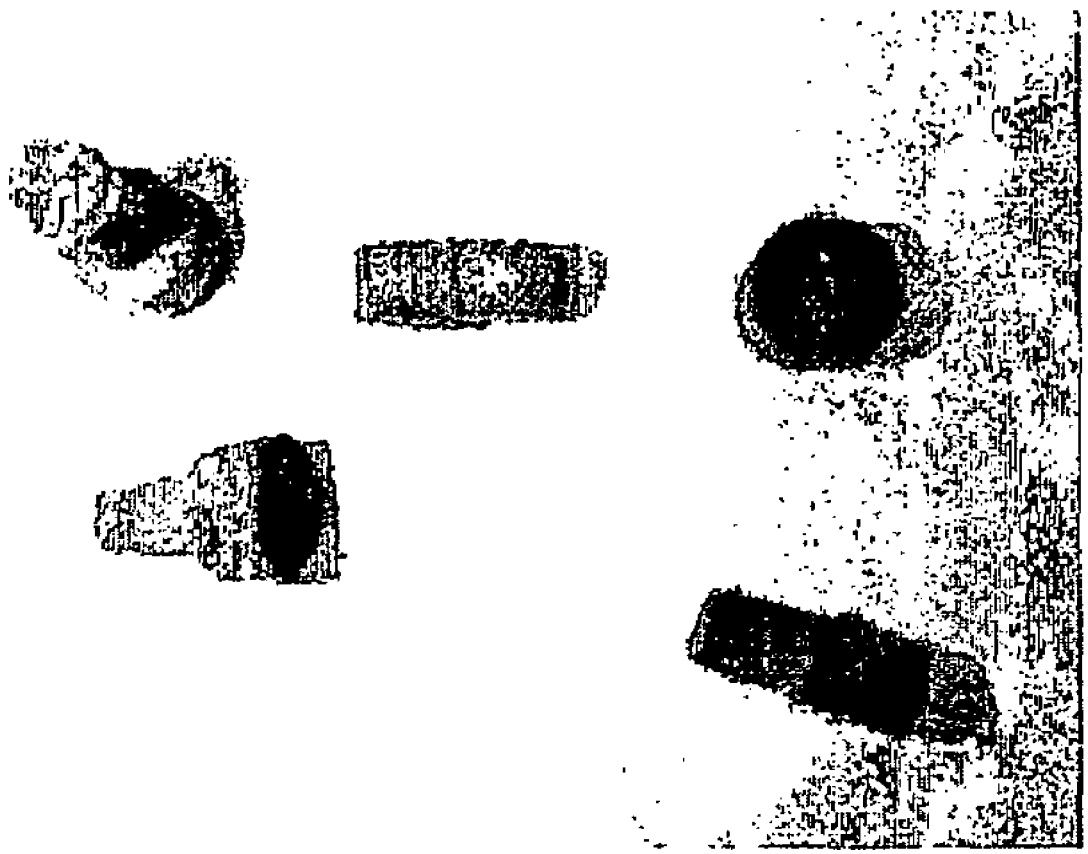
FIG. 3. Extruded parts of various geometries made from gluten biopolymer.
Figure 4:
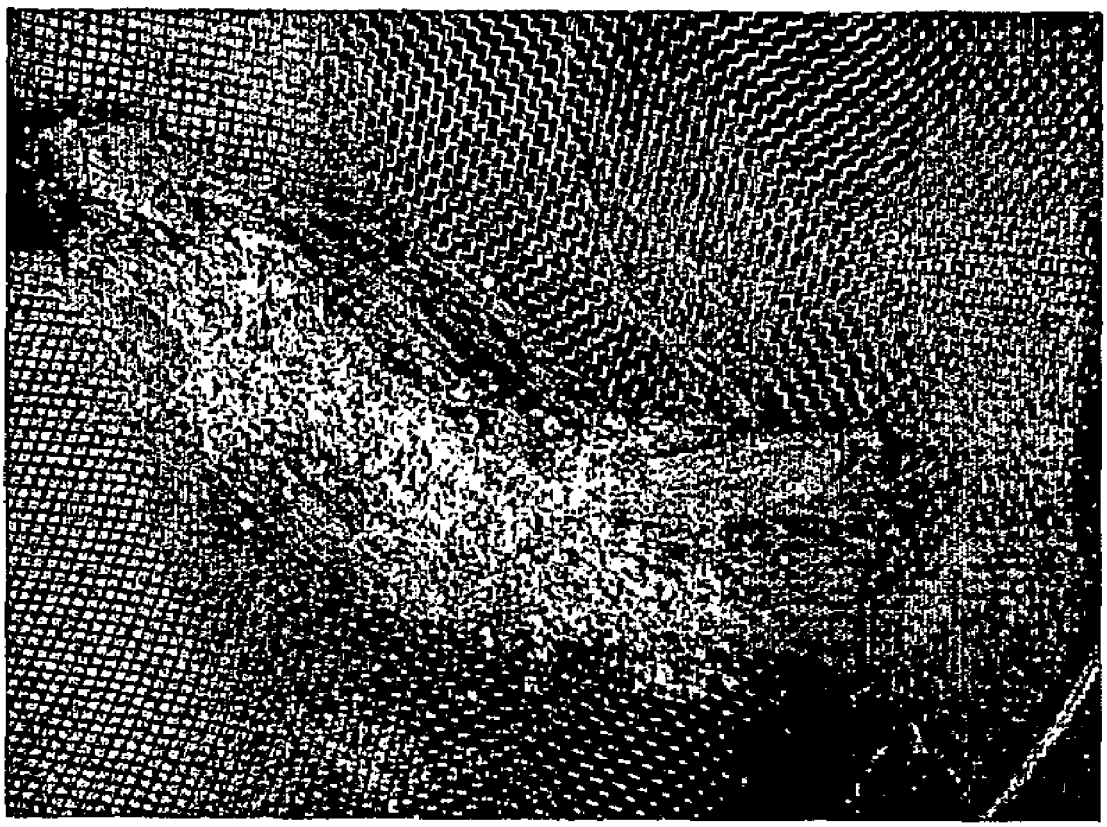
FIG. 4. A photograph of flax fibers covered with gluten powder, for illustrative purposes only. In the actual experiment, the flax fibers were coated manually by rolling them in the gluten powder. Afterwards, a strainer was used to support the gluten powder-coated fibers as they were immersed in a 45° C. alkaline (pH=11) water bath for 30 seconds.
Figure 5:
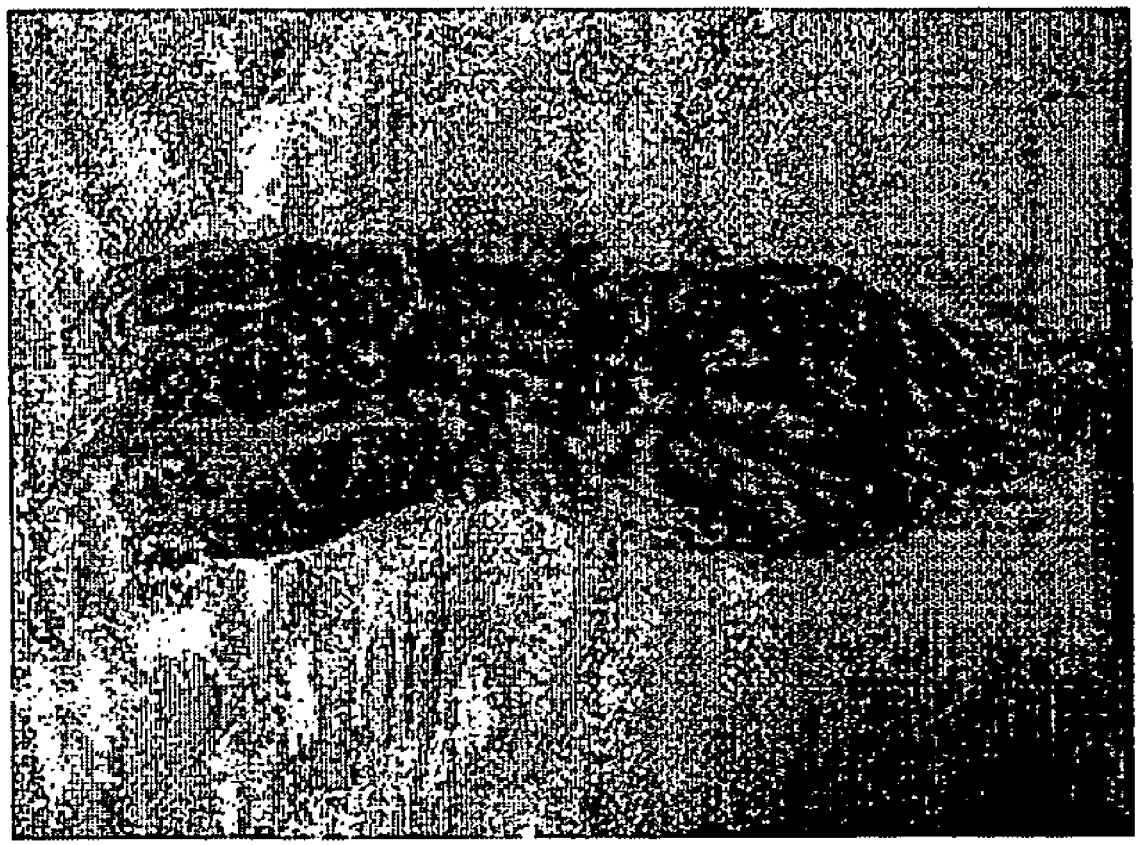
FIG. 5. A photograph of the gluten biopolymer/flax fiber bundle composite formed after the gluten polymer formed a precipitate around the flax fibers. After two days, the gluten matrix was rigid, as most of the moisture inside the gluten polymer network had evaporated.
Figure 6:
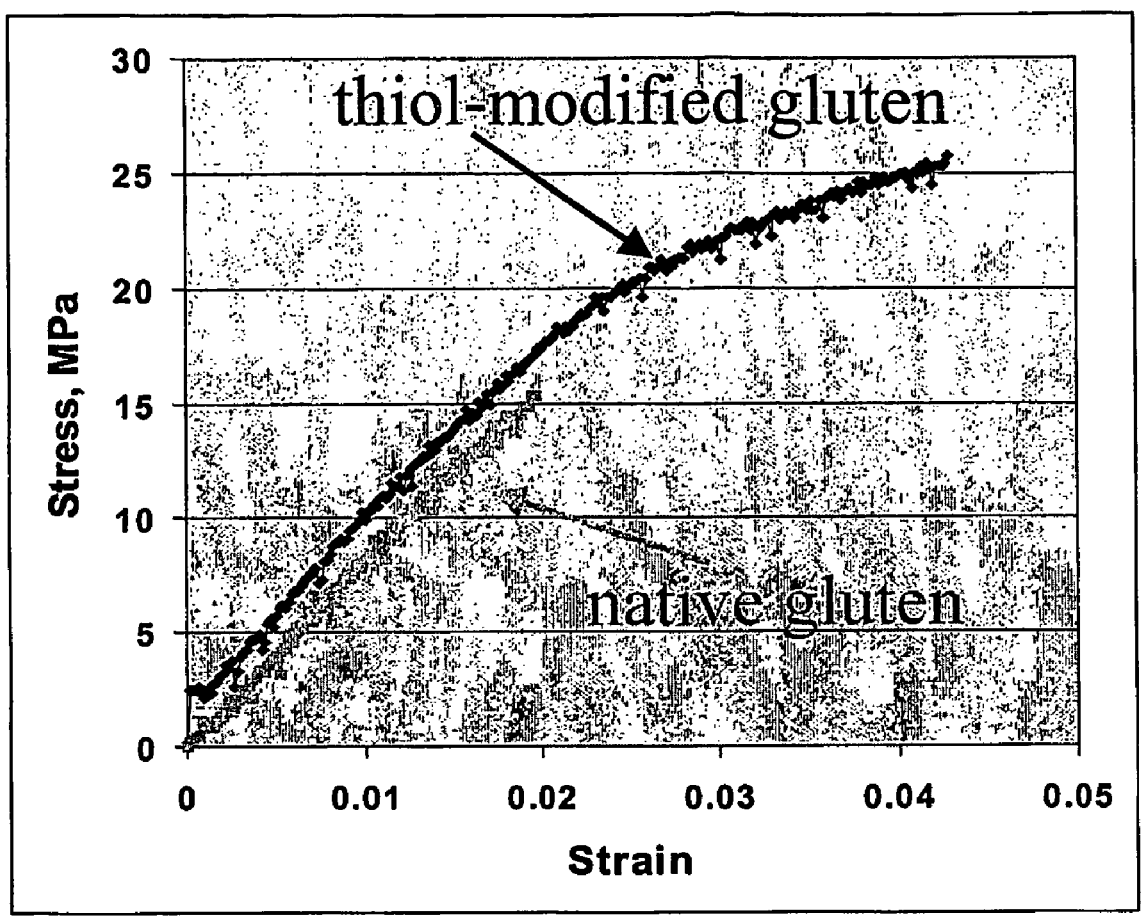
FIG. 6. Comparison of mechanical properties of native gluten (sample 20) and thiol-modified gluten (sample 22).
Figure 7:
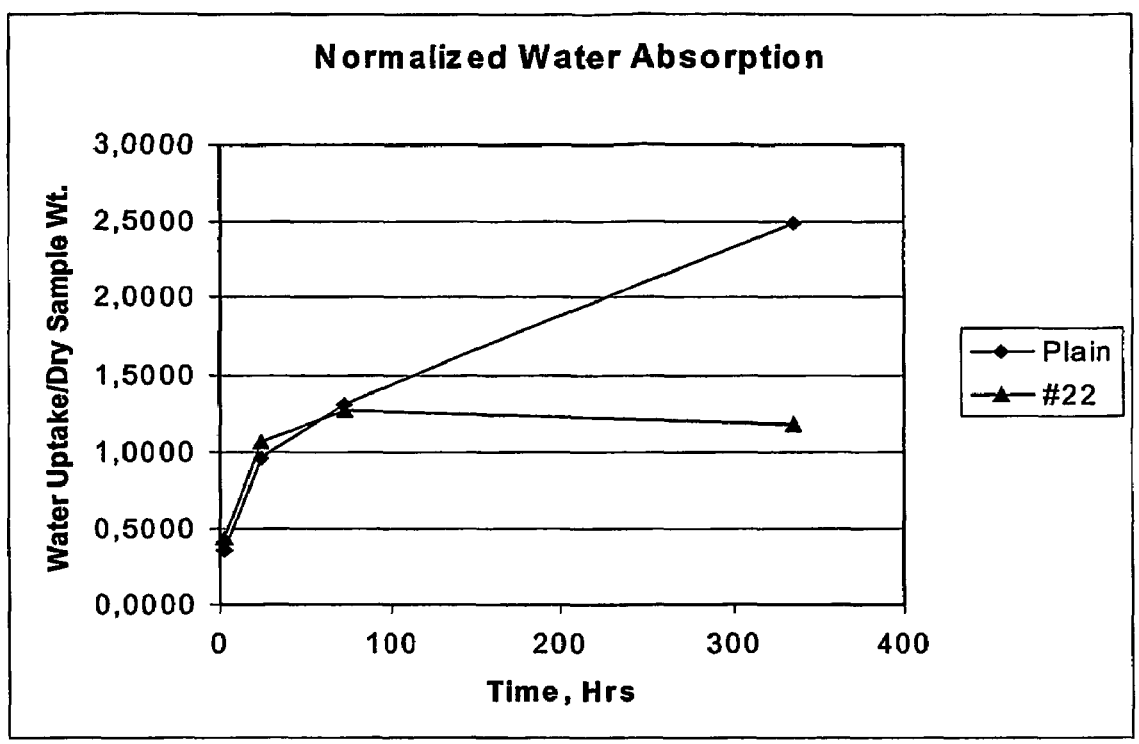
FIG. 7. Water absorption measurements with plain gluten and preparation 22 (as described in example 6). The data indicate a difference in molecular structure between the plain gluten and the thiol-treated gluten.

Results of the research showed that when a thiol-containing molecule was used in the preparation of the gluten polymer and incorporated into the network structure of the gluten polymer, material's strain-to-failure and strength can be increased without compromising stiffness (FIGS. 10, 11 and 12). Furthermore, water absorption results indicate that the presence of a thiol-containing molecule leads to an increase in molecular crosslink density (FIG. 7). Finally, HPLC data of molded thiol-modified gluten are consistent with that of a polymer that has been further crosslinked (FIG. 8).

The improved strain and strength of polymers of the present invention and obtained by the process of the present invention can be deduced from experiments performed. Comparing samples prepared with polythiol-containing molecules wath native molded gluten or even samples prepared with cysteine, shows an increase in strength and strain, and even more when stress and strain would be looked at together.

Another important aspect is that the results show that there is a certain ageing effect that further improves the mechanical properties of the new gluten biopolymer (FIGS. 9, 10, 11 and 12). Mechanical studies showed that ageing the powdered gluten formulations for two or three to six months leads to an increase in both strength and strain-to-failure of molded specimens. This can be observed through direct comparison between the set of unmodified and modified specimens molded and tested in the spring (April-June) with the second series of specimens, which were molded and tested around 3 months later during the summer (July-August) as shown in FIGS. 9a and b and 10, 11 and 12. Both sets of specimens were molded from the same set of powders formulated in the February to April time period. In general, the results show that the modified wheat gluten polymer has properties approaching that of polypropylene and epoxies, which could very well continue to improve with time.

The research also resulted in the development of gluten biopolymer-modified fiber (flax or glass) and bundle, demonstrating a process to make fully biodegradable composite materials. Qualitative analysis suggests that a strong interface between the natural fibers and biopolymer matrix can form spontaneously under the proper conditions, precluding the need to rely on more traditional chemical treatments to promote fiber/matrix adhesion. The present methods that are descroed in literature mostly can only handle short fibers (maximally approximately 2-3 cm). This method is able to handle long fibers. Some molding techniques as used in U.S. Pat. No. 5,665,152 (injection molding) are not able to handle long fibers.

In order to be able to chemically modify gluten or to coat gluten on fibers, gluten needs to be dispersed. Several methods for the preparation of chemically modified gluten or gluten coated fibers described, use a dispersion of gluten. Several methods and agents can be used to obtain a dispersion of gluten:

(Mild) acidic/alkaline conditions: Probably the most gentle way to disperse gluten, is to bring the gluten in an aqueous environment at a relatively low pH. Decreasing the pH (to around 4 or lower, with for example dilute HCl, (dilute) acetic acid or lactic acid) allows to solubilize a part of the gluten proteins and surely allows to make a homogenous "dispersion" of the total gluten. Also alkaline conditions (e.g. aqueous NaOH) allow to make a homogenous dispersion.

However, stong alkaline or acid conditions will further help solubilizing gluten but will affect the protein structure (deamidation, modification of some amino acids, peptide bond hydrolysis, etc.).

An advantage of dispersing under (mild) acidic or alkaline conditions is that proteins can be precipitated by a simple change in pH towards neutral where gluten proteins are totally insoluble. This type of precipitation can than be applied after putting fibers in a gluten dispersion to make the gluten proteins efficiently stick to the fiber material.

Aqueous alcohol solutions: Alcohol/water mixtures are very often used in gluten research to solubilize part of the gluten proteins (ca 50% can be solubilized) and the total gluten can be homogenously dispersed in alcohol/water mixtures. Mixture of 70% ethanol or 50% propanol can for example be applied for this purpose. Some other proteins, like for example corn zeins (the "gluten" equivalent from corn) are soluble in pure methanol.

The fact that gluten proteins are only soluble/dispersible at certain alcohol concentrations offers the possibility to precipitate them by changing this concentration (adding more alcohol or by dilution with water). The alcohol can also be removed by evaporation.

aiding agents: Several agents are often used in gluten research either in pure water or in one of the above solvents to aid solubilization of gluten proteins. Often several agents are combined to solubilize gluten proteins. However, protein structure is nearly always affected in this way.

Following aiding agents are used:
a/ reducing agents (e.g. sulfites, cysteine, glutathione, dithiothreitol): by lowering the molecular weight of the proteins they enhance their solubility (obviously they also drastically change their structure and functionality)
b/ hydrogen bond breakers (e.g. urea)
c/ chaotropic agents (e.g. guanidinium hydrochloride)
d/ detergents (e.g. sodium dodecyl sulfate, cetyl trimethyl ammonium bromide)
e/ salts: increasing the ionic strength is known to decrease the solubility of gluten proteins.

However, in the literature it can also be found that incubation of gluten in salt would subsequently increase the solubility of gluten proteins in distilled deionized water.

other solvents: Literature describes the use of other solvents (e.g. ketones, amide solvents) for these purposes (e.g. solubilization of zeins).

Drying of materials can be performed in several ways as known in the art. Materials can be dried on the air, with hot air, by using spray-drying or freeze-drying. The materials can also be placed in an dessiccator or a heating gun, combined with water attracting compounds. The solvents in a mixture can furthermore also be evaporated by using a rotovapor, or by applying vacuum. Spray-drying can for example be performed under the following conditions: compressed air P=4 bars; inlet T=130° C. and outlet T=95-105° C.

The fluidized bed technology can also be used in the invention in order to pre-coat the fibers with gluten. With for example ETI's E-Preg® process, carbon fiber or fiberglass fabric is passed through a special electrostatic fluidized bed coater capable of depositing (gluten) powder on both sides of the web. Electrostatic attraction causes the powder to adhere to the substrate, which is then passed through an oven to melt and flow the powder into or onto the fiber.

General Methods and Materials

Commercial wheat gluten from Amylum (Aalst, Belgium) was used in this study. The protein content of this gluten can be determined with the Dumas method or the Kjeldahl-method.

Preparation of a New Gluten Biopolymer by Using Thiol-Containing Molecules

The chemical modification of gluten can in general be obtained through mixing gluten with a thiol-containing molecule in an aqueous medium. By subsequent compression molding a material with modified properties is obtained.

The thiol-containing molecules were added in amounts calculated with respect to the experimentally determined cysteine content in the gluten (gluten contains approximately 13.8 mmol thiol function—this can be derived from the amount of cysteine in gluten). As an example, the principle of a 1:1 stoichiometric mixture can be applied to allow one mole of TP200 3MP3 SH groups to interact with one mole of gluten cysteine groups. The basic procedure involved preparing a gluten dispersion containing the thiol-containing compound and leaving the mixture to stir overnight, mostly in a refrigerator (6-8° C.). The following day the contents were dried (i.e. freeze-dried) over a certain period (i.e. four days). Afterwards, the dried contents were homogenized using a mortar and pestle, passed through a micron-size sieve, and put on a rotating shaker overnight. Specific details pertaining to individual samples are provided below.

Compression Molding—Thermo Molding

Compression molding was performed with reference gluten samples, thiol-modified gluten and gluten coated fibers to produce a molded material. Specimens and gluten samples can be compression molded by applying a certain pressure and temperature, i.e. at 5 bars/150° C. for 3 to 15 min. Specimens were prepared in a 10 cavity mold. The mold was carefully prepared using a mold release agent, previously applied and cured before gluten powders were used.

Preparation of Gluten Coated Fibers

The general method used in order to obtain a gluten coated fiber was to bring the fiber into contact with gluten in a gluten-dispersing mixture (first pre-coating the fiber with gluten in the dry state and than contacting with a gluten-dispersing mixture or mixing fibers with gluten in a gluten-dispersing mixture). In one method the gluten is pre-coated with gluten powder by bringing gluten in contact with the fibers, for example by sprinkling or by the fluidized bed method.

Mechanical Properties Determination

Tensile Test: The 10 specimens prepared from each molding exercise were used in tensile tests. Specimens were tested within 1 hour of molding, after 24 hours, and after 7 days. At each testing time, 3 of the specimens were used. All specimens were stored at ambient conditions so the tests after 24 hours and after 7 days provide preliminary indications of temporal stability of the material. The tests were conducted on a computer interfaced Instron 1011 with a 1000 Lb load cell. Load data were collected at a rate of 10 s$^{-1}$, and each test was repeated 3 times. The stress strain curves were evaluated to provide modulus, failure strain, and yield strength. Modulus was determined by fitting a straight line to the stress strain curves in the early region at strains below ½%.

Charpy Impact test: For the measurement of fracture toughness, the Charpy impact test was conducted in accordance with ISO-Norm 179.

Three point bend test: the three point bend test was performed as described in literature and is well known to a person skilled in the art.

Water absorption studies: the water absorption studies were performed as described in literature and is well known to a person skilled in the art Molecular Weight Determination: Size Exclusion—High Performance Liquid Chromatography (SE-HPLC)

Samples were dissolved (1 mg/ml) in 0.05M sodium phosphate buffer (pH 6.8), containing 2.0% (w/v) sodium dodecyl sulphate (SDS), filtered (0.45 μm) and a fraction was loaded on a Phenomenex BioSep-SEC-S4000 (300 mm×7.8 mm) column (Phenomenex, Torrance, Calif., USA). The proteins were eluted at room temperature with 50% (v/v) acetonitrile containing 0.05% (v/v) trifluoroacetic acid (flow rate: 0.5 ml/min). Reduced protein samples were obtained by adding 1% (w/v) dithiothreitol to the phosphate-SDS buffer. The detection was performed with a Kontron HPLC 332 detector (Kontron Instruments Ltd, Buckinghamshire, UK) at 210 nm. Proteins were classified into three groups: insoluble polymeric protein, soluble polymeric protein, and monomeric protein. The proportion of insoluble protein was calculated from peak areas of reduced and unreduced samples in the chromatograms (Verbruggen, I. M. et al., *J. Cereal Sci.* 2003, 37, p. 151).

EXAMPLES

Comparison of the mechanical properties of plain gluten (e.g. impact strength) with those of several synthetic materials, comprising polypropylene, epoxy, low-density polyethylene (PE), and high-density polyethylene PE can be found in the literature (Table 1).

TABLE 1

Mechanical properties of various polymers as they compare with gluten matrix material processed at 150° C./72 bars as measured by the Three-Point-Bend test.

| Polymer | Charpy Impact Strength (kJ/m$^2$) |
|---|---|
| Gluten | 2.48 |
| Polypropylene | 14 |
| Epoxy | 7.5 |
| Low density PE | 39 |
| High density PE | 68 |

According to the literature the apparent E-modulus and tensile strength of wheat gluten seems on par with a number of commonly used synthetic polymers. However, a drawback is the fact that the impact strength of cured gluten is relatively low. The impact strength increased when glycerol was added to the matrix, however this results in the lowering of the E-modulus and tensile strength.

The different examples that are given and the data presented are clearly varying with the concentration of thiol-containing molecules and the time before molding and time before measuring ("ageing effects").

Example 1

The polythiol-containing molecule, 'TP200 3MP3', was employed in this example. Gluten powder (150 g) was added slowly (over a period of 1½ hrs at room temperature) to 1.5 L 0.05 M acetic acid solution containing 0.1% (w/w) of 'TP200 3MP3'. The mixture was stirred continuously as the gluten powder was added to the solution. The dispersion was put on a shaker in a refrigerator and left overnight. A homogenous dispersion of the gluten proteins in dilute acetic acid was obtained, enabling the 'TP200 3MP3' molecule to interact directly with the gluten proteins. The material was recovered by precipitation upon increasing the pH (from 4-4.5 to 6.5-7) by addition of dilute NaOH. Afterwards, the gluten/solvent mixture was separated by centrifugation (10,000 g, 20° C., 15 min) and the modified-gluten precipitate was dried and stored in a refrigerator until further use. The molded material could than be obtained by compression molding the previously prepared powder.

Example 2

In this experiment, a 50% (w/w) propanol-water solution was used in place of dilute acetic acid, and the solvent was evaporated by 'rotavapping' the modified-gluten/solvent mixture at 50° C. However, subsequent removal of the dried biopolymer from the glass flask was difficult due to the strong adhesion between the gluten network and the glass. To be able to easily remove the biopolymer dilute acetic acid can be added, before all the propanol is evaporated. Upon incorporating 0.1% (w/w) of 'TP200 3MP3' in a 50% (v/v) propanol-water solution, the fracture toughness of molded gluten was increased from 3 kJ/m$^2$ to an average of 36 kJ/m$^2$ as measured by the Charpy Impact test. Specimens were compression-molded at 150° C./25 bars for 10 min. and subsequently cooled to 20° C. over a period of 5 min. Individual fracture toughness measurements of four six-day-old TP2003MP3-modified gluten specimens yielded an average value of 36.2 kJ/m$^2$, with a deviation of around 10 kJ/m$^2$. An unmodified control sample yielded a Charpy impact strength of 3.2 kJ/m$^2$ (Iso Norm 179 standard analysis).

Example 3

Preparation and Investigation of Gluten Coated Flax Fibers

A bundle of flax fiber was pre-coated with gluten powder by sprinkling the gluten powder onto the fibers, which was then placed between two metal strainers. A dilute alkaline (NaOH) water bath was prepared (as acidic conditions are known to be detrimental to flax fibers). Two strainers were used to contain the coated fiber bundle, which was then dipped in the alkaline water bath for 30-60 sec. The hydrated gluten formed a precipitate almost immediately, resulting in a gluten-encapsulated fiber bundle. The gluten-coated fiber bundle was left to dry in ambient conditions for a period of several days and yielded the new composite material, namely gluten coated flax fiber. The gluten coated fibers remain intact after several months.

Example 4

Preparation of Gluten Coated Glass Fibers

For the purpose of preparing the gluten coated glass fibers, the standard "Fiber-Tow Impregnation Line" or "Fluidized Bed" technology was applied. In this experiment, a commercial grade-glass fiber: "2400 P 319 E1" from Owens Corning was used. The airflow of the fluidized chamber was set at 0.2 bars and the vibration at 7 bars. The oven temperatures were set at 120-170° C. and 175° C., respectively, and the rollers inside the oven were removed. The oven was not used to melt the gluten, but merely, to dry the fibers. As the gluten powder coated fiber was drawn from the fluidized bed, water was applied manually using either a water bath or a squirt bottle for bringing the gluten molecules in close proximity with the fiber surface.

Example 5

Chemically Modified Gluten Polymers Prepared During Experiments with their Referred Sample Numbers 1) plain gluten; solvent used 0.05M AcOH; contents freeze-dried, milled, and passed through a 250 micron sieve
2) gluten+1% (w/w) TP703MP3; solvent used: 0.05 M AcOH; contents freeze-dried, milled, and passed through a 250 micron sieve
3) gluten+1% (w/w) TP200 3MP3; solvent used: 0.05 M AcOH; contents freeze-dried, milled, and passed through a 250 micron sieve
4) gluten+5.8% (w/w) TP200 3MP3; solvent used: 0.05 M AcOH; contents freeze-dried, milled, and passed through a 250 micron sieve
5) gluten+1% (w/w) TP200 3MP3; solvent used 50% PrOH; contents freeze-dried, and homogenized with a mortar and pestle
6) plain gluten; solvent used 70% EtOH; contents freeze-dried (twice), homogenized with a mortar and pestle, passed through a 400 micron sieve, and put on rotating shaker overnight
7) gluten+0.1% (w/w) DTT; solvent used: 70% EtOH; contents freeze-dried (twice), homogenized with a mortar and pestle, passed through a 400 micron sieve, and put on rotating shaker overnight
8) gluten+0.1% (w/w) DTT+0.5% (w/w) $KIO_3$ (present in excess); solvent used 70% EtOH; contents freeze-dried (twice), homogenized with a mortar and pestle, passed through a 400 micron sieve, and put on rotating shaker overnight
9) gluten+0.1% (w/w) DTT+1% (w/w) TP200 3MP3+0.5% (w/w) $KIO_3$ (present in excess); solvent used: 70% EtOH; contents freeze-dried (twice), homogenized with a mortar and pestle, passed through a 400 micron sieve, and put on rotating shaker overnight
10) gluten+0.1% (w/w) DTT+1% (w/w) TP200 3MP3; solvent used: 70% EtOH; contents freeze-dried (twice), homogenized with a mortar and pestle, passed through a 400 micron sieve, and put on rotating shaker overnight
11) plain gluten; solvent used 70% EtOH; contents freeze-dried (twice), homogenized with a mortar and pestle, passed through a 400 micron sieve, and put on rotating shaker overnight.
18) gluten+6.5% (w/w) China reed fibers; solvent used 0.05M AcOH; contents freeze-dried (twice), homogeneous on a macroscopic scale; mortar and pestle not used to avoid fiber breakage
19) gluten+29.4% (w/w) China reed fibers; solvent used 0.05M AcOH; contents freeze-dried (twice), inhomogeneous on a macroscopic scale; mortar and pestle not used to avoid fiber breakage
20) plain gluten; solvent used 0.05 M AcOH; contents freeze-dried, homogenized with a mortar and pestle, passed through a 400 micron sieve, and put on rotating shaker overnight
21) gluten+0.55% (w/w) cysteine; solvent used 0.05 M AcOH; contents freeze-dried, homogenized with a mortar and pestle, passed through a 400 micron sieve, and put on rotating shaker overnight
22) gluten+5.8% (w/w) TP200 3MP3; solvent used 0.05 M AcOH; contents freeze-dried, homogenized with a mortar and pestle, passed through a 400 micron sieve, and put on rotating shaker overnight
23) gluten+3.2% (w/w) TP70 3MP3; solvent used 0.05 M AcOH; contents freeze-dried, homogenized with a mortar and pestle, passed through a 400 micron sieve, and put on rotating shaker overnight
24) gluten+3.2% (w/w) TP70 3MP3+0.5% $KIO_3$; solvent used 0.05 M AcOH; contents freeze-dried, homogenized with a mortar and pestle, passed through a 400 micron sieve, and put on rotating shaker overnight
25) plain gluten; solvent used 0.05 M AcOH; contents freeze-dried, homogenized with a mortar and pestle, passed through a 400 micron sieve, and put on rotating shaker overnight
26) gluten+1.7% (w/w) cysteine; solvent used 0.05 M AcOH; contents freeze-dried, homogenized with a mortar and pestle, passed through a 400 micron sieve, and put on rotating shaker overnight
27) gluten+1.0% (w/w) DTT; solvent used 0.05 M AcOH; contents freeze-dried, homogenized with a mortar and pestle, passed through a 400 micron sieve, and put on rotating shaker overnight
28) gluten+11.6% (w/w) TP200 3MP3; solvent used 0.05 M AcOH; contents freeze-dried, homogenized with a mortar and pestle, passed through a 400 micron sieve, and put on rotating shaker overnight
29) gluten+11.2% (w/w) TP200 polyol; solvent used 0.05 M AcOH; contents freeze-dried, homogenized with a mortar and pestle, passed through a 400 micron sieve, and put on rotating shaker overnight 30) plain gluten; solvent used 0.05 M AcOH; contents freeze-dried, homogenized with a mortar and pestle, passed through a 400 micron sieve, and put on rotating shaker overnight
31) gluten+5×[5.8% (w/w) TP200 3MP3]; solvent used 0.05 M AcOH; contents freeze-dried, homogenized with a mortar and pestle, passed through a 400 micron sieve, and put on rotating shaker overnight
32) gluten+10×[5.8% (w/w) TP200 3MP3]; solvent used 0.05 M AcOH; contents freeze-dried, homogenized with a mortar and pestle, passed through a 400 micron sieve, and put on rotating shaker overnight
33) gluten+15×[5.8% (w/w) TP200 3MP3]; solvent used 0.05 M AcOH; contents freeze-dried, homogenized with a mortar and pestle, passed through a 400 micron sieve, and put on rotating shaker overnight Example 6

Results of Experiments

The strain, strength and stiffness of several samples has been measured. Results are shown in FIGS. 9, 10, 11, and 12. The results show an increase in strain and strength, while the stiffness remains unaffected for thiol-modified gluten polymers and for gluten-coated fibers.

The invention claimed is:

1. A polymer of gluten comprising gluten proteins, wherein said gluten proteins are intermolecularly covalently linked through polythiol-containing molecules.

2. The polymer of claim 1, which has a strength higher than 30 MPa.

3. A composite material comprising fibers and a gluten polymer intermolecularly covalently linked through polythiol-containing molecules according to claim 1.

4. A process for preparing a composite material comprising fibers and a gluten polymer, wherein the process comprises the steps of:
 (a) pre-coating said fibers with the gluten polymer of claim 1; and
 (b) contacting the pre-coated fibers obtained under (a) with a gluten-dispersing mixture.

5. The process of claim 4, comprising a final step of drying the material obtained after step (b), ageing said material by leaving said material unhandled for a certain time period, and then compression-moulding said material.

6. A process for preparing a polymer of gluten comprising gluten proteins comprises the step of mixing said gluten proteins in a gluten-dispersing mixture with polythiol-containing molecules.

7. The process of claim 6, wherein said gluten-dispersing mixture is an aqueous environment.

8. The process of claim 6, comprising the step of isolating said gluten polymer by precipitation and subsequent centrifugation.

9. The process of claim 6, comprising the step of drying said gluten-dispensing mixture comprising said gluten proteins so as to obtain a dried material.

10. The process of claim 9, comprising the step of first ageing said dried material by leaving it unhandled for a certain time period and then compression-moulding said dried material.

11. The process of claim 10, wherein said time period is at least 7 days.

12. The process of claim 10, wherein said time period is at least 30 days.

13. The process of claim 10, wherein said time period is about 30 days to about 90 days.

14. The process of claim 10, wherein said ageing is performed at room temperature.

15. The process of claim 10, wherein said ageing is performed at a temperature of over 25° C.

16. The process of claim 10, wherein said ageing is performed at a temperature higher than 40° C.

17. A process for preparing a gluten based polymer comprising the steps of:
 (a) mixing gluten in a gluten-dispersing mixture together with polythiol-containing molecules;
 (b) drying the mixture resulting therefrom so as to obtain dried material;
 (c) ageing said dried material by leaving it unhandled for a certain time period; and
 (d) compression-moulding said dried material or a selection or combination thereof.

18. The process of claim 17 which comprises a step of precipitating the reaction products out of the mixture by mixing gluten in a gluten-dispersing mixture together with polythiol-containing molecules and thereafter the step of centrifuging said mixture before drying the precipitate.

* * * * *